United States Patent [19]
Srivastava et al.

[11] Patent Number: 5,929,037
[45] Date of Patent: Jul. 27, 1999

[54] MODIFIED α-D-GLCp-(1-2)-α-D-GLCp-(1-3)-α-D-GLCp-ANALOGUES

[75] Inventors: Om Srivastava; Roman Szweda, both of Edmonton, Canada

[73] Assignee: Alberta Research Council, Edmonton, Canada

[21] Appl. No.: 08/485,057

[22] Filed: Jun. 7, 1995

[51] Int. Cl.$^6$ ............................. A61K 31/70; C07H 15/00
[52] U.S. Cl. ........................ 514/25; 536/4.1; 536/17.2; 536/17.3; 536/17.6; 536/17.9; 536/18.1
[58] Field of Search .................. 536/4.1, 17.2, 536/17.3, 17.6, 17.9, 18.1; 574/25

[56] References Cited

U.S. PATENT DOCUMENTS

| | | | |
|---|---|---|---|
| 5,079,353 | 1/1992 | Ratcliffe et al. | 536/53 |
| 5,438,124 | 8/1995 | Matta et al. | 536/4.1 |

FOREIGN PATENT DOCUMENTS

| | | |
|---|---|---|
| 0 173 948 | 3/1986 | European Pat. Off. . |
| 0 422 975 | 4/1991 | European Pat. Off. . |

OTHER PUBLICATIONS

Neverova, et al., *Anal. Biochem.*, 222:190–195 (1994).
Gallo et al., *Science*, 220:865 (1983).
Barre–Sinoussi et al., *Science*, 220:868 (1983).
Montagnier et al., *Science*, 144:283 (1985).
McDougal et al., *Science*, 231:382 (1986).
Allan et al., *Science*, 228:1091 (1985).
Ratner et al., *Nature*, 313:277 (1985).
Matthews et al., *Proc. Natl. Acad. Sci. USA*, 84:5424 (1987).
Pal et al., *Proc. Natl. Acad. Sci. USA*, 86:3384 (1989).
Gruters, et al., *Nature*, 330:74 (1987).
Stanecloni et al., *Trends. Biochem. Sci.*, 4:65 (1979).
Parodi et al., *Biochem. Biophys. Acta.*, 559:1 (1978).
Kornfield et al., *J. Biol. Chem.*, 253:7771 (1978).
Frommer et al., *Planta Med.*, 35:195 (1979).
Saul et al., *Biochem. Biophys. Acta.*, 221:593–597 (1983).
Romero et al., *Biochem. J.*, 226:733 (1985).
Schweden et al., *Arch. Biochem. Biophys.*, 248:335 (1986).
Takeo et al., *Carbohydr. Res.*, 162:95 (1987).
Takeuchi et al., *J. Biol. Chem.*, 108:42–46 (1990).
Shailubhai et al., *Biochem. J.*, 247:555 (1987).
Bause et al., *FEBS Lett.*, 206(2):208 (1986).
Szumilo et al., *Arch. Biochem. Biophys.*, 247:261 (1986).
Alvarado et al., *Biochem.*, 30(4):881 (1991).
Lemieux et al., *Journal of the American Chemical Society*, 97:14 (1975).
Fugedi et al., *Glycoconj. J.*, 4:97 (1987).
Pozsgay, et al. *J. Org. Chem.*, 53:4042 (1988).
Dasgupta et al., *Carbohydr. Res.*, 177:C13 (1988).
Kallin et al., *Glycoconj. J.*, 5:37 (1988).
Birberg et al., *J. Carbohydr. Chem.*, 8:47 (1989).
Classon et al., *J. Carbohydr. Chem.*, 8:543 (1989).
Nilsson et al., *J. Carbohydr. Chem.*, 8:613 (1989).
Peters et al., *Can. J. Chem.*, 67:497 (1989).
Reddy et al., *Tetrahedron Lett.*, 30:4283 (1989).
Paulsen, *Angew Chem. Int. Ed. Engl.*, 21:155 (1982).
Norberg et al., *J. Carbohydr. Chem.*, 7:283 (1988).
Kovac et al., *Carbohydr. Res.*, 184:87 (1988).
Sato et al., *Carbohydr. Res.*, 115:C6 (1986).
Koike et al., *Carbohydr. Res.*, 163:189 (1987).
Jain et al., Meeting Society for Complex Carbohydrates, Ann Arbor, MI. Nov. 8–11 (1989) Abstr. 160.
Nakahara et al., International Chemical Congress of Pacific Basin Societies, Honolulu, Hawaii (1989) Abstr. BIOS 0410.
Herscouvics et al., *J. Biol. Chem.*, 252:2271 (1987).
Saunier et al., *J. Biol. Chem.*, 257: 14155 (1982).
Feizi, et al., *Glycobiology*, 1(1):17–23 (1990).
Takeuchi, et al., *Chem. Pharm. Bull.*, 38(7):1970–1972 (1990).
Shimizu, et al., *AIDS*, 4:975–979 (1990).
Tan, et al., *J. Biol. Chem.*, 266(22):14504–14510 (1991).
Bause, et al., *FEBS Letters*, 278(2):167–170 (1991).
Ishida, et al., *Carb. Research*, 208:267–272 (1990).
Okamoto, et al., *Tetrahedron*, 46(17):5835–5857 (1990).
Abbas, et al., *Proc. Japanese–German Symp. Berlin*, pp. 20–21 (1988).
Schmidt, *Agnew. Chem. Int. Ed. Eng.*, 25:212–235 (1986).
Kameyama, et al., *Carbohydr. Res.*, 209:$C_1$–$C_4$ (1991).

*Primary Examiner*—Elli Peselev
*Attorney, Agent, or Firm*—Burns, Doane, Swecker & Mathis, L.L.P.

[57] ABSTRACT

Disclosed is the trisaccharide α-D-Glcp-(1-2)-α-D-Glcp-(1-3)-α-D-Glcp and compounds related thereto as well as pharmaceutical compositions thereof.

14 Claims, 5 Drawing Sheets

| Compound No. | $R^{10}$ | $R^{11}$ | $R^{12}$ | $R^{13}$ | $R^{14}$ | $R^{15}$ |
|---|---|---|---|---|---|---|
| 6 | Br | H | OBn | OBn | OBn | OBn |
| 7 | Br | H | OAllyl | OBn | OBn | OBn |
| 8 | Br | H | F | OBn | OBn | OBn |
| 9 | H | SBn | H | OBn | OBn | OBn |
| 10 | SBn | H | H | OBn | OBn | OBn |
| 11 | Br | H | $N_3$ | OAc | OAc | OAc |
| 12 | Br | H | OMe | OBn | OBn | OBn |
| 13 | Br | H | OBn | H | OBn | OBn |
| 14 | Br | H | OBn | OMe | OBn | OBn |
| 15 | Br | H | OBn | OBn | H | OBn |
| 16 | Br | H | OBn | OBn | OMe | OBn |
| 17 | H | OAc | OAc | OAc | OAc | H |
| 18 | OAc | H | OAc | OAc | OAc | H |
| 19 | H | SBn | OAc | OAc | OAc | H |
| 20 | H | SBn | OH | OH | OH | H |
| 21 | H | SBn | OBn | OBn | OBn | H |

34

35

| Comp. No. | R⁶ | R⁷ | R⁸ | R |
|---|---|---|---|---|
| 23 | OBn | OBn | CH₂OBn | OBn |
| 24 | OBn | OBn | CH₂OBn | F |
| 25 | OBn | OBn | CH₂OBn | H |
| 26 | OAc | OAc | CH₂OAc | N₃ |
| 27 | OH | OH | CH₂OH | N₃ |
| 28 | OBn | OBn | CH₂OBn | OMe |
| 29 | H | OBn | CH₂OBn | OBn |
| 30 | OMe | OBn | CH₂OBn | OBn |
| 31 | OBn | H | CH₂OBn | OBn |
| 32 | OBn | OMe | CH₂OBn | OBn |
| 33 | OBn | OBn | CH₃ | OBn |

+ β-isomer (37)

36

38

39

| Compound No. | $R^6$ | $R^7$ | $R^8$ | R |
|---|---|---|---|---|
| 40 | OH | OH | $CH_2OH$ | OH |
| 41 | OH | OH | $CH_2OH$ | F |
| 42 | OH | OH | $CH_2OH$ | H |
| 43 | OH | OH | $CH_2OH$ | $NH_2$ |
| 44 | OH | OH | $CH_2OH$ | OMe |
| 45 | H | OH | $CH_2OH$ | OH |
| 46 | OMe | OH | $CH_2OH$ | OH |
| 47 | OH | H | $CH_2OH$ | OH |
| 48 | OH | OMe | $CH_2OH$ | OH |
| 49 | OH | OH | $CH_3$ | OH |

MODIFIED α-D-GLCp-(1-2)-α-D-GLCp-(1-3)-α-D-GLCp-ANALOGUES

BACKGROUND OF THE INVENTION

1. Field of the Invention

This invention relates to the field of oligosaccharides. In particular, the invention is directed to the trisaccharide α-D-Glcp-(1-2)-α-D-Glcp-(1-3)-α-D-Glcp and compounds related thereto as well as pharmaceutical compositions thereof.

2. References

The following references are cited as superscript numbers at the relevant point of reference in the text.

[1] Gallo et al., *Science*, 220:865 (1983).
[2] Barre-Sinoussi et al., *Science*, 220:868 (1983).
[3] Montagnier et al., *Science*, 144:283 (1985).
[4] McDougal et al., *Science*, 231:382 (1986).
[5] Allan et al., *Science*, 228:1091 (1985).
[6] Ratner et al., *Nature*, 313:277 (1985).
[7] Matthews et al., *Proc. Natl. Acad. Sci. USA*, 84:5424 (1987).
[8] Pal et al., *Proc. Natl. Acad. Sci. USA*, 86:3384 (1989).
[9] Gruthers, et al., *Nature*, 330:74 (1987).
[10] Stanecloni et al., *Trends. Biochem. Sci.*, 4:65 (1979).
[11] Parodi et al., *Biochem. Biophys. Acta.*, 559:1 (1978).
[12] Kornfield et al., *J. Biol. Chem.*, 253:7771 (1978).
[13] Frommer et al., *Planta Med.*, 35:195 (1979).
[14] Saul et al., *Biochem. Biophys. Acta.*, 221:265 (1983).
[15] Romero et al., *Biochem. J.*, 226:733 (1985).
[16] Schweden et al., *Arch. Biochem. Biophys.*, 248:335 (1986).
[17] Takeo et al., *Carbohydr. Res.*, 162:95 (1987).
[18] Takeuchi et al., *J. Biol. Chem.*, 108:42 (1990).
[19] Shailubhai et al., *Biochem. J.*, 247:555 (1987).
[20] Bause et al., *FEBS Lett.*, 206(2) (1986).
[21] Szumilo et al., *Arch. Biochem. Biophys.*, 247:261 (1986).
[22] Eugenio et al., *Biochem.*, 30(4): (1991)
[23] Lemieux et al., *J.A.C.S.*, 97:14 (1975).
[24] Fugedi et al., *Glycoconj. J.*, 4:97 (1987).
[25] Pozsgay, et al., *J. Org. Chem.*, 53:4043 (1988).
[26] Dasgupta et al., *Carbohydr. Res.*, 177:C13 (1988).
[27] Kallin et al., *Glycoconj. J.*, 5:37 (1988).
[28] Birberg et al., *J. Carbohydr. Chem.*, 8:47 (1989).
[29] Classon et al., *J. Carbohydr. Chem.*, 8:543 (1989).
[30] Nillson et al., *J. Carbohydr. Chem.*, 8:613 (1989).
[31] Peters et al., *Can. J. Chem.*, 67:497 (1989).
[32] Reddy et al., *Tetrahedron Lett.*, 30:4283 (1989).
[33] Paulsen, *Agnew Chem. Int. Ed. Engl.*, 21:155 (1982).
[34] Norberg et al., *J. Carbohydr. Chem.*, 7:283 (1988).
[35] Kovac et al., *Carbohydr. Res.*, 184:87 (1988).
[36] Sato et al., *Carbohydr. Res.*, 115:C6 (1986).
[37] Koike et al., *Carbohydr. Res.*, 163:189 (1987).
[38] Jain et al., *Meeting Society for Complex Carbohydrates*, Ann Arbor, Mich. November 8–11 (1989) Abstr. 160.
[39] Nakahara et al., *International Chemical Congress of Pacific Basin Societies*, Honolulu, Hi. (1989) Abstr. BIOS 0410.
[40] Hercouvics et al., *J. Biol. Chem.*, 252:2271 (1987).
[41] Saunier et al., *J. Biol. Chem.*, 257: 14155 (1982).
[42] Feizi, et al., *Glycobiology*, 1(1):17–23 (1990)
[43] Takeuchi, et al., *Chem. Pharm. Bull.*, 38(7):1970–1972 (1990)
[44] Shimizu, et al., *AIDS*, 4:975–979 (1990)
[45] Tan, et al., *J. Biol. Chem.*, 266(22):14504–14510 (1991)
[46] Bause, et al., *FEBS Letters*, 278(2):167–170 (1991)
[47] Ishida, et al., *Carb. Research*, 208:267–272 (1990)
[48] Okamoto, et al., *Tetrahedron*, 46(17):5835–5837 (1990).
[49] Abbas, et al., *Proc. Japanese-German Symp. Berlin*, pp. 20–21 (1988).
[50] Paulsen, *Agnew. Chem. Int. Ed. Eng.*, 21:155–173 (1982).
[51] Schmidt, *Agnew. Chem. Int. Ed. Eng.*, 25:212–235 (1986).
[52] Fugedi, et al., *Glycoconj. J.*, 4:97–108 (1987).
[53] Kameyama, et al., *Carbohydr. Res.*, 209:$C_1$–$C_4$ (1991).
[54] Ratcliffe, et al., U.S. Pat. No. 5,079,353.

The above references are incorporated herein by reference in their entirety to the same extent and in the same manner as if each individual reference was specifically and individually incorporated by reference in its entirety.

STATE OF THE ART

Glucosidase inhibitors have been shown to display antiviral activities.[45] For example, human immunodeficiency virus type 1, (HIV-1), the retrovirus[1,2] responsible for acquired immunodeficiency syndrome (AIDS), contains two heavily glycosylated envelope proteins, gp120 and gp41, which mediate attachment of virions to glycosylated cell surface receptor molecules ($CD_4$ antigens). The viral glycoproteins and host $CD_4$ surface receptors play an important role in viral adsorption, penetration, syncytium formation and spread of the virus to adjacent cells[3,4].

Carbohydrates comprise approximately 50% of the total mass[5,6] of gp120 with all 24 sites that contain the concensus N-glycosylation being glycosylated.[42] Carbohydrate moieties are known to be involved in the recognition of $CD_4$ antigens by gp120. For example, purified gp120 can be used to temporarily block cell fusion and the formation of syncytia. However, the use of non-glycosylated gp120 reduces the binding of $CD_4$ and the blocking of cell fusion by only fifty percent[7].

The trimming reactions catalyzed by the glycosidases can be blocked by specific inhibitors. These inhibitors fall in two categories. The indolizidine alkaloids castanospermine and swainsonine inhibit glucosidase I and mannosidase II, respectively. The nojirimycins and related structures also inhibit trimming glycosidases: nojirimycin, 1-deoxynojirimycin (dNM), and N-methyl-1-deoxynojirimycin are glycosidase inhibitors.

The processing of oligosaccharides on gp120 via the so-called "trimming pathway" is directly linked to viral infectivity[8,9]. Inhibitors of glycoprotein processing enzymes have been used to prevent the trimming reactions, and result in altered glycoproteins that are implicated in breaking the virus replication cycle. The inhibitors are therefore, antiviral (including anti-HIV) therapeutic agents. The strategy of glycosylation based inhibitors is of enormous potential utility because virtually all viruses, which must replicate in human cells, require their coat glycoproteins to be correctly glycosylated in order to retain the ability to infect the host.

Glycosylation of asparagine residues in proteins occurs by transfer of the precursor dolichol derivative[10,11] of oligosaccharide[12] $Glc_3Man_9GlcNAc_2$, i.e. $Glc_3Man_9GlcNAc_2$-PP-Diol. A series of trimming reactions are involved in processing. The first trimming reaction (FIG. 1) occurs in rough endoplasmic reticulum where the outermost α-(1-2) linked distal glucose residue is cleared by the action of glucosidase I enzyme. The removal of two α-(1-3) linked glucose residues gives the immediate precursor of high-mannose glycoproteins. Mannosidase I activity then removes the four α-(1-2) linked mannose residues within the Golgi complex. Addition of N-acetylglucosamine, removal by a mannosidase II of two α-(1-3) and α-(1-6) linked mannose residues, and the addition of distal sugars such as galactose, N-acetylglucosamine, fucose and sialic acid residues by the corresponding glycosyltransferases, completes the process.

There has been much effort to find inhibitors of glucosidase or mannosidase "trimming enzymes", owing to their potential as therapeutic (antiviral) agents. Nojirimycin[13], deoxynojirimycin[13], castanospermine[14] and several analogues of these compounds have been reported in the literature as glucosidase inhibitors[15,16]. Additionally, due to their glucosidase inhibition, these compounds have been disclosed for limiting digestion of dietary carbohydrates by inhibition of intestinal α-glucosidases thereby providing a regimen for treating diabetes mellitus and obesity[43]. However, deoxynojirimycin appears to require a concentration of at least 1 mmol/l to induce the inhibitory effect in vitro and such high doses might cause side-effects in vivo.[44]

The trisaccharide, α-D-Glcp-(1-2)-α-D-Glcp-1,3-α-D-Glcp ("trisaccharide"), i.e., O-α-D-glucopyranosyl-(1-2)-O-α-D-glucopyranosyl-(1-3)-α-D-glucopyranose, corresponds to the outer trisaccharide unit of the lipid-linked oligosaccharide chain which is involved in the biosynthesis of asparagine-linked glycoproteins, $(Glc)_3Man_9GlcNAc_2$. The synthesis of this trisaccharide was carried out by Takeo et al.[17]. Modification of the trisaccharide indicates that these are features important to recognition by the enzyme glucosidase I.

It would be desirable to replace existing glycosylation inhibitors, e.g., castanospermine and deoxynojirimycin, by agents of lower toxicity, greater specificity and superior binding capacity for use as either anti-viral agents or in the treatment of diabetes mellitus and/or obesity.

SUMMARY OF THE INVENTION

This invention is directed to oligosaccharides which are modified analogues of the trisaccharide, α-D-Glcp-(1-2)-α-D-Glcp-(1-3)-α-D-Glcp. The oligosaccharides within the scope of the invention are glucosidase inhibitors or intermediates in the production of glucosidase inhibitors and can be used as anti-viral agents and/or in the treatment of obesity and/or diabetes mellitus.

Accordingly, in one of its composition aspects, this invention is directed to compounds represented by Formulas I–III. The compounds of Formulas I–II are novel compounds used in the synthesis of glucosidase inhibitors whereas the compounds of Formula III are novel glucosidase inhibitors.

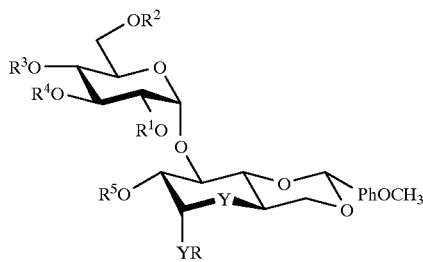

I wherein each Y is independently —O— or —NH—, R is an aglycon of at least 1 carbon atom, $R_1$ is selected from the group consisting of —$CH_2CH=CH_2$ or hydrogen, and $R^2$, $R^3$, $R^4$ and $R^5$ are protecting groups differentially removed as compared to —O—$CH_2CH=CH_2$;

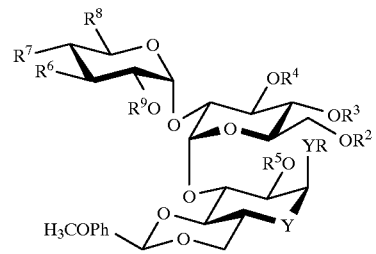

II wherein each Y is independently —O— or —NH—, R is an aglycon of at least one carbon atom, $R^6$ and $R^7$ are independently selected from the group consisting of —O—Pr, hydrogen, fluoro, azido, and —$OCH_3$ where Pr is a protecting group, $R^8$ is selected from the group consisting of —O—Pr, fluoro, azido and —$OCH_3$ where Pr is a protecting group, and $R^9$ is selected from the group consisting of hydrogen or a protecting group.

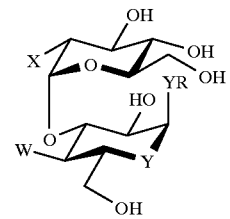

III wherein each Y is independently O or —NH— and X is selected from the group consisting of valienamine, validamine, valiolamine, 5-deoxy-5-thioglucose, homonorijimycin, 1,5-trans-(C)-glucopyranosylamine and a compound of the formula:

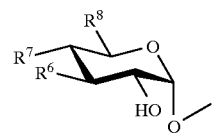

wherein $R^6$, $R^7$ and $R^8$ are as defined above and W is selected from the group consisting of hydrogen, hydroxyl, alkoxy of from 1 to 4 carbon atoms, fluoro, chloro, and amino.

This invention is further directed to pharmaceutical compositions which compositions comprise a pharmaceutically acceptable carrier and a therapeutic effective amount of a compound of formula III above.

BRIEF DESCRIPTION OF THE DRAWINGS

FIG. 2 illustrates monosaccharide and disaccharide compounds 2, 3, 4, 5 and 22; whereas FIG. 3 illustrates monosaccharides 6, 7, 8, 9, 10, 11, 12, 13, 14, 15, 16, 17, 18, 19, 20, and 21.

DESCRIPTION OF PREFERRED EMBODIMENTS

Figure 1:
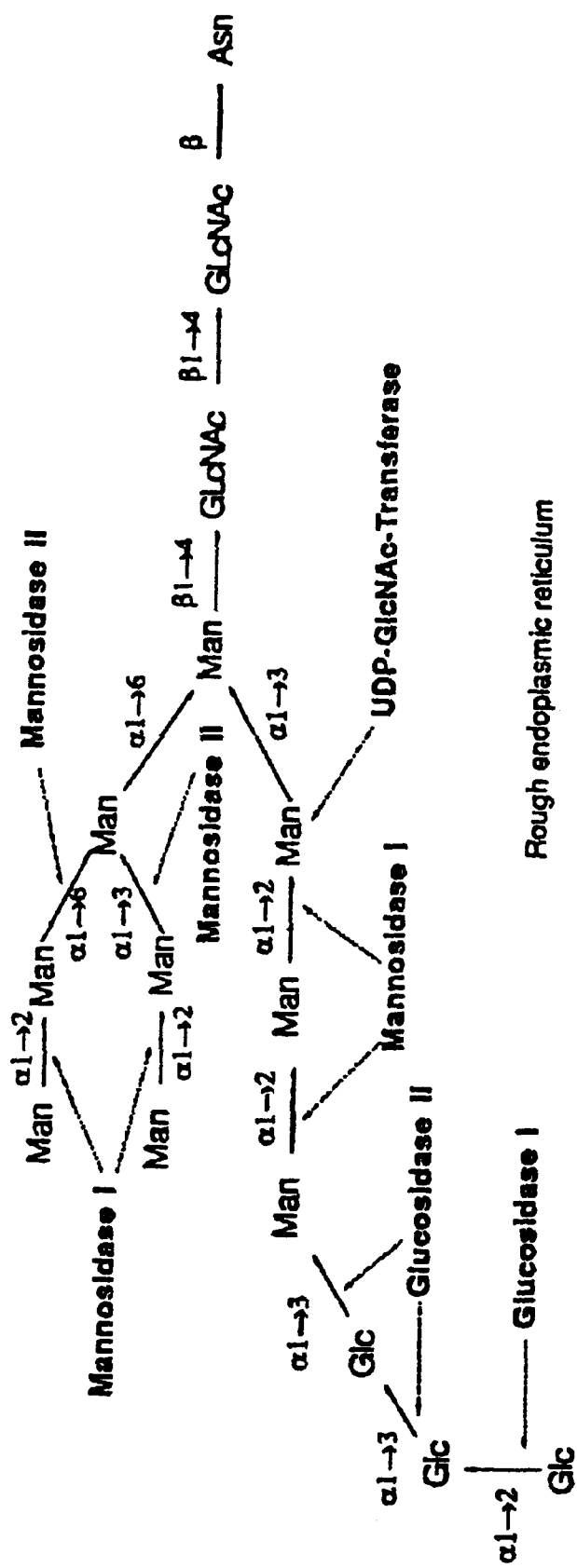
FIG. 1 illustrates the composite structure $Glc_3Man_9GlcNAc_2$ transferred from dolichylpyrophosphate to asparagine residues of the glycoprotein with trimming sites.

This invention is directed to the discovery of novel modified analogues of the trisaccharide found at the end of the precursor dolichol derivative of the oligosaccharide transferred in the glycosylation of asparagine residues in protein, i.e. Glc$_3$Man$_9$GlcNAc$_2$-PP-Diol. During cell processing, the trisaccharide's glucose residues are trimmed by glucosidase I.

This trisaccharide has been synthesized as an aglycon (e.g., 8-methoxycarbonyloctyl derivative) and the terminal and reducing end glucose residue can be modified. For example, each hydroxyl group of the terminal glucose residue has been altered in several ways to determine the important terminal glucose hydroxy groups in the binding to glucosidase I, and the alterations which give the greatest reduction in glucosidase I activity.

Modifications to the trisaccharide include substitution of a single —OH group at the 2" —OH position with fluoro, deoxy, methoxy and amino functionalities. Other hydroxy groups on the terminal saccharide can likewise be replaced with hydrogen, methoxy, fluoro, deoxy, and amino functionalities. The terminal (non-reducing) glucose unit can also be replaced by valienamine, validamine, valioamine, 5-deoxy-5-thioglucose, homonojirimycin, 1,5-trans-(C)-glucopyranosylamine group as described below.

Conformational studies[22] of the propyl derivative of a related tetrasaccharide α-D-Glcp-(1-2)-α-D-Glcp-(1-3)-α-D-Glup-(1-3)-α-D-Manp, indicate the 2" —OH group of the terminal glucose is involved in a strong hydrogen bond with the 4—OH of Mannose bearing glucose. Molecular modeling based on this information supports our view of the biochemical function in the trisaccharide unit. We find that replacement of the 2" —OH group of the trisaccharide by F, —OCH$_3$, H and —NH$_2$ gives loss of activity and therefore this hydroxyl group is essential for binding to glucosidases, especially glucosidase I. On the other hand, the 3", 4" and 6" positions of the terminal glucose are available for modification leading to glucosidase inhibitors of formula III above. Before discussing the invention in further detail, the following terms will be defined.

Definitions

As used herein, the following terms have the meaning given below:

The term "trisaccharide" unless otherwise noted, refers to the glucotriose, α-D-Glcp-(1-2)-α-D-Glcp-(1-3)-α-D-Glcp.

The term "an enveloped virus" refers to a virus the surface of which is extensively covered by carbohydrate, in particular, glycoprotein. Glycoprotein is carbohydrate in the form of an array of oligosaccharide structures attached to the polypeptide backbone. The acquired immune deficiency syndrome (AIDS) is caused by enveloped viruses (e.g., HIV-1).

The term "oligosaccharide" refers to a carbohydrate structure having from 2 to about 7 saccharide units (disaccharides, trisaccharides, etc.). The particular saccharide units employed are not critical, and include, by way of example, all natural and synthetic derivatives of glucose. In addition to being in their pyranose form, all saccharide units within the scope of this invention are preferably in their D form. The oligosaccharide chains are added to the glycoprotein and variously processed by enzymes of the host cell.

The term "glycosylation" refers to the enzymatic process in which oligosaccharides are added to glycoproteins.

The term "glucosidase I" or "α-glucosidase I" refers to a specific enzyme which participates in glycosylation of the HIV glycoprotein, gp120.

The term "glucosidase inhibitors" refers to naturally occurring and synthetic compounds of diverse chemical structure which interfere with the processing of oligosaccharides by glycosidase enzymes. Likewise, the term "inhibitors of α-glucosidase I" refers to naturally occurring and synthetic compounds of diverse chemical structure which interfere with processing of oligosaccharides by glucosidase I. Certain inhibitors of glucosidase I are oligosaccharides.

The term "modified analogues of trisaccharide" or "modified trisaccharide" refers to molecules which retain the O-α-D-glucopyranosyl-(1-2)-O-α-D-glucopyranosyl-(1-3)-D-glucopyranose structure, but contain at least one substituent which differs from that of the trisaccharide. That is, the trisaccharide has been chemically modified so as to introduce and/or remove one or more functionalities from the trisaccharide. For example, such modification can result from the removal of an OH functionality, the introduction of an amine functionality, the introduction of an azido or halo functionality, the replacement of the ring ether with an amino group, and so forth.

In this connection, a modification of particular interest and usefulness is the insertion of an aglycon functionality at the carbon 1 position of the α-D-glucopyranoside ring of the trisaccharide, or other suitable ring location useful in conjugation of the moieties prepared according to the methods of this invention.

The aglycons are non-saccharide groups containing at least one carbon atom, generally found in the oligosaccharide structures in the 1-position of the reducing sugar, (i.e., —YR). In general, Y is selected from the group consisting of oxygen and —NH—, and R is an aglycon of at least 1 carbon atoms. Preferably, R is selected from the group consisting of —(A)—Z wherein A represents a bond, an alkylene of from 2 to 12 carbon atoms, a moiety of the formula —(CH$_2$—CR'G)$_n$— where n is an integer of from 1 to 5, R' is selected from the group consisting of H, methyl and ethyl, and G is selected from the group consisting of H, halogen, phenyl and substituted phenyl, and a moiety of the formula —(CH$_2$—CR'R'G')$_n$— where R' and n are as defined above and G' is selected from the group consisting of oxygen, sulfur and NR'; Z is selected from the group consisting of H, methyl, thenyl, nitrophenyl, aminophenyl, and when A is an alkylene group or a moiety of the formula —(CH$_2$—CR'G)$_n$—, Z is also selected from the group consisting of —OH, —SH, —NHR", —NR"$_2$, —C(O)OH, —C(O)OR", —C(O)NH$_2$, —C(O)NH—NH$_2$, —C(O)NHR", —C(O)NR"$_2$ and —OR'" where R" is independently alkyl of from 1 to 4 carbon atoms and R'" is an alkenyl of from 3 to 10 carbon atoms.

In one embodiment, the aglycon can be selected to link the oligosaccharides described herein to a solid support and when so selected, the aglycon functions as a chemical linker. Such solid support bound oligosaccharides can be used to isolate glucosidase I. When so employed, the linkers are bifunctional with one functional group (e.g., —OH or —NH$_2$) covalently linking the aglycon to the oligosaccharide and the other functional group covalently linking the aglycon to the solid supports. Examples of such other functional groups on bifunctional linkers are well known in the art. Specific examples of chemical linkers include —OC$_6$H$_4$pNO$_2$, —OCH$_2$CH$_2$SCH$_2$CO$_2$CH$_3$, —OCH$_2$CH$_2$SC$_6$H$_4$—pNH$_2$, —O(CH$_2$)$_6$NHCOCF$_3$, —CH$_2$CH=CH$_2$, —OCH$_2$CH$_2$NHC(O)(CH$_4$)$_4$CO$_2$CH$_3$, —(CH$_2$)$_8$COOCH$_3$, —(CH$_2$CH$_2$O)$_2$CH$_2$CH=CH$_2$, —O(CH$_2$)$_3$S(CH$_2$)$_2$NH$_2$, —(CH$_2$)$_5$OCH$_2$CH=CH$_2$, and —(CH$_2$)$_8$CH$_2$OH.

Certain of these linkers carry "masked" functional groups which permits demasking at the appropriate point in the synthesis. For example, with —OC$_6$H$_4$pNO$_2$, the nitro group is reduced to a functional amino group by conventional methods thereby demasking this functional group. Likewise, with —O(CH$_2$)$_6$NHCOCF$_3$, the trifluoroacetamido protecting group can be removed unmasking the primary amino group which can then be used for coupling. Allyl aglycons can be derivatized in the presence of 2-aminoethanethiol to provide for an aglycon —OCH$_2$CH$_2$CH$_2$SCH$_2$CH$_2$NH$_2$ which can be coupled to the solid support via the free amino group.

The selection of a particular chemical linker is a matter of convenience rather than of preference.

The chemical linker is sometimes referred to herein as the "aglycon". Consequently, the term "chemical linker" and "aglycon" are often interchanged. However, it is understood that the term "chemical linker" is a subset of aglycons because not all aglycons carry bifunctional groups permitting them to be covalently bound to a solid support. On the other hand, oligosaccharides with aglycons derived from a monofunctional hydrophobic group (e.g., HO(CH$_2$)$_{12}$CH$_3$) can be used to separate glucosidases from a solution containing such glucosidases and the resulting adduct can then be recovered, for example, by incorporation into a liposome advantageously using this hydrophobic group.

Preferred aglycons have from 1 to 20 carbon atoms and more preferably 1 to 10 carbon atoms. Particularly preferred aglycons include hydrophobic aglycons having 6–20 carbon atoms which can enhance the uptake and release as well as cellular distribution of the oligosaccharides in vivo.[45,47]

The term "protecting group" or "blocking group" refers to any group which when bound to one or more hydroxyl or amino groups of the oligosaccharide prevents reactions from occurring at these hydroxyl or amino groups and which protecting group can be removed by conventional chemical or enzymatic steps to reestablish the hydroxyl group or amino group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced either enzymatically or chemically onto a hydroxyl functionality and later selectively removed either by enzymatic or chemical methods in mild conditions compatible with the nature of the product. Preferred removable amino blocking groups include conventional substituents such as t-butyoxycarbonyl (t-BOC), benzyloxycarbonyl (CBZ), and the like.

In some embodiments, one blocking group is selected to be differentially removed from another blocking group. Such differential removal refers to the fact that the removal conditions for a first blocking group have little effect on the other blocking group which remains intact after removal of the first blocking group. For example, a hydroxyl group blocked with a benzyl protecting group can be differentially removed from a hydroxyl group blocked with an acetyl blocking group since the hydrogenation conditions used to remove the benzyl protecting will have little effect on the acetyl blocking group.

The term "modified trisaccharide α-glucosidase I inhibitors" refers to modified trisaccharides which are glucosidase I acceptors, preferably with lower toxicity, greater specificity and superior binding capability than the trisaccharide.

The term "intermediate useful in the synthesis of modified trisaccharide α-glucosidase I inhibitors" refers to those modified saccharides which are converted to α-glucosidase I inhibitors by reactions and reaction schemes within the skill of the art.

The term "salts" includes the addition salts of the oligosaccharides capable of forming salts and are derived from a variety of organic and inorganic counter salts well known in the art and include, by way of example only, sodium, potassium, calcium, magnesium, ammonium, tetralkylammonium, and the like. Such salts can also be formed by the addition of inorganic or organic acids to the compounds described herein including, by way of example, HCl, HBr, H$_2$SO$_4$, acetic acid, propionic acid, etc. Preferably, the salt is a pharmaceutically acceptable salt.

For the purposes of this application, all sugars are referenced using conventional three letter nomenclature. All sugars are assumed to be in the D-form unless otherwise noted, except for fucose, which is in the L-form. Further all sugars are in the pyranose form.

Methodology

Chemical methods for the synthesis of the oligosaccharides described herein are known in the art. These oligosaccharides are generally assembled using suitably protected individual monosaccharides and suitably protected individual disaccharides intermediates.

The specific methods employed are generally adapted and optimized for each individual structure to be synthesized. In general, the chemical synthesis of all or part of these oligosaccharide first involves formation of a glycosidic linkage on the anomeric carbon atom of the reducing sugar. Specifically, an appropriately protected form of a naturally occurring or of a chemically modified glucose structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possess one free hydroxyl or primary/secondary amino group at the position where the glycosidic linkage is to be established. A large variety of aglycon moieties are known in the art and can be attached with the proper configuration to the anomeric center of the reducing unit. Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature. See, for example, Okamoto et al.[48], Abbas et al.[49], Paulsen[50], Schmidt[51], Fugedi et al.[52], Kameyama et al.[53] and Ratcliffe, et al.[54]

In the same manner, an pseudo sugar containing a —NH— in the pyranose sugar structure can be introduced in the reducing sugar end of the oligosaccharide merely by use of suitable blocking groups well known in the art.

In one preferred embodiment for the synthesis of oligosaccharide glycosides (each Y=O ), a convenient synthetic block disaccharide intermediate 8-methoxycarbonyloctyl-2-O-benzyl-4,6-O-p-methoxybenzylidene-3-O-(2-O-allyl-3,4,6-tri-O-benzyl-α-D-glucopyranosyl)-α-D-glucopyranoside 4 from which the allyl group was removed provides the key alcohol for synthesizing various modified trisaccharide structures. Alcohol 5 was utilized for glycosylation reaction with 6, 8, 12, 13, 14, 15, 16 and 22 under copper bromide-DMF catalyzed reaction conditions providing blocked trisaccharides 23, 24, 28, 29, 30, 31, 32, 34 and 35. Reaction of 5 with thioglycosides 9, 10 and 21 under the conditions mentioned above, provided blocked trisaccharides 25 and 33. However, using mercuric bromide and mercuric cyanide as a catalyst, compound 5 was coupled with bromide 11 to provide 26. Deprotection by conventional methods provided trisaccharides in appropriate yields.

Figure 3:
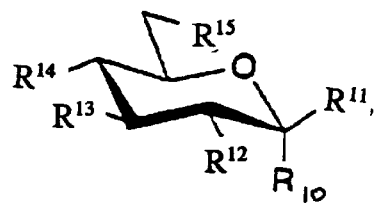

The synthesis of Compounds 6–22 are reported in Examples 4–20 below and FIG. 3 recites the structure of each of these monosaccharides.

Figure 2:
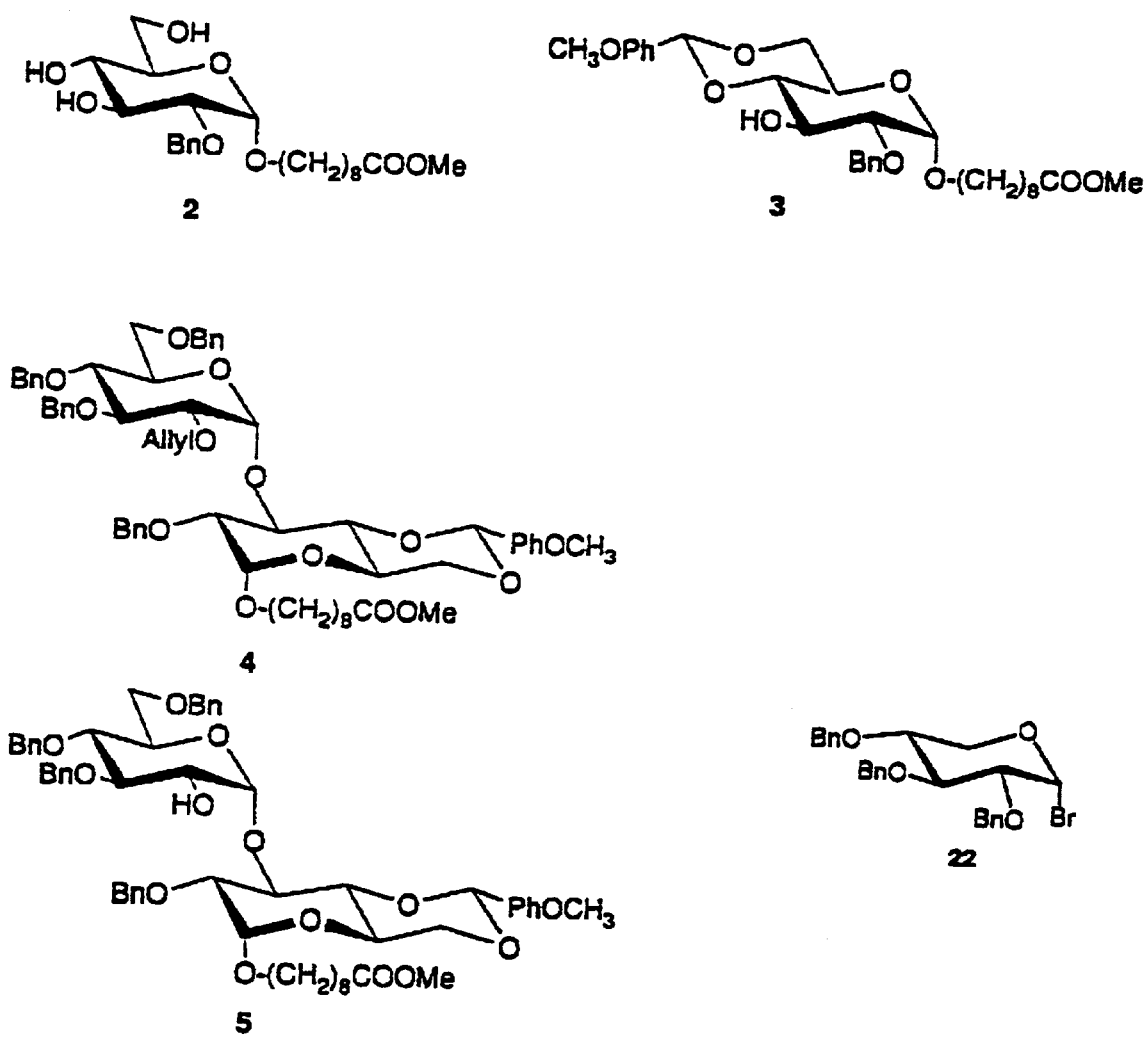
FIGS. 2 and 3 illustrate key monosaccharide and disaccharide intermediates. Specifically.

Referring to FIG. 2, the key disaccharide alcohol 5 was prepared in three straightforward steps from the readily accessible 8-methoxycarbonyl-octyl-2-O-benzyl-α-D-glucopyranoside 2, which was converted into the p-methoxy-4,6-O-benzylidene derivative 3 by treatment with p-methoxy-benzaldehyde dimethyl acetal in the presence of catalytic p-toluene sulfonic acid. Compound 3 was glycosylated with 2-O-allyl-3,4,6-tri-O-benzyl-α-D-glucopyranosyl bromide 7 under standard halide ion catalyzed reaction conditions[23] (tetraethylammonium bromide, DMF, molecular sieves) to provide the fully protected disaccharide 4 (90%). Deallylation involved isomerization of 2-O-allyl ether of 4 by tris-triphenylphosphine rhodium (I) chloride and 1,4-diazabicyclo[2.2.2]octane in ethanol-benzene-water (7:3:1) followed by hydrolysis of the vinyl ether with mercuric chloride and mercuric oxide to give the alcohol 5 in 81% yield.

For further chain elongation, 6-deoxy-tetra-O-benzyl-α-D-glucopyranose derivative 21 was synthesized by treatment with 6-deoxy-tetra-O-acetyl-α,β-glucopyranose 17,18 with benzylmercaptan using boron-trifluoroetherate as a catalyst to provide 19, followed by deacetylation to give 20 and benzylation with benzyl bromide and sodium hydride in dimenthylformamide.

The synthesis of blocked trisaccharides was attempted by glycosylation conditions reported in the literature, e.g., halide ion catalyzed glycosylation. However, yield under such circumstances was poor even if the reaction was carried out for a week using five equivalents of glycosyl bromides.

The use of thioglycosides as glycosyl donors in oligosaccharide synthesis has been reviewed by P. Fugedi et al[24]. A first possibility is the "one step activation" with thiophylic reagents such as TfOMe, DMTST[24], NOBF$_4$[25], MST[26] and SOCl$_2$/CF$_3$SO$_3$H[27]. Excellent results have been reported by using these approaches[28-31]. A "one step remote activation" of heterocyclic thioglycoside has been reported to provide α-glycosides in excellent yields[32]. The other alternate is a "two step activation" procedure whereby the glycosyl halide, first generated in the presence of bromide or chloride is then activated by the usual halophilic reagents [33,34,35].

The formation of glycosides by activation of 1-thioglycosides in the presence of CuBr$_2$—(C$_4$H$_9$)$_4$N$^+$Br$^-$ complex and of an appropriate promoter in various solvents introduced by Ogawa has been reported to be a two step activation procedure. This approach has been shown to be efficient in the synthesis of α-galactosides[36,37], α-fucosides[38] and α-xylosides[39]. The wide range of experimental conditions used in this type of glycosylation, which can be done in the presence or absence of (C$_4$H$_9$)$_4$N$^+$Br$^-$, in polar or nonpolar solvents or mixtures of the two, and because Cu(II) salts easily form complexes with a wide variety of compounds, indicates that each individual glycosylation would require optimization of a number of parameters.

Our results indicate that a CuBr$_2$-DMF complex is by itself, very efficient in promoting (i) the formation of the glycosyl bromide from the benzyl thioglycoside, (ii) a reaction of α-glycosylation of a substrate for either 1-thioglycoside or the glycosyl bromide. Our trisaccharide syntheses show that CuBr$_2$-DMF complex is a very efficient catalyst in the reaction of α-glycosylation, similar to "halide ion catalyzed glycosylation" extended to other promoters by H. Paulson, using CuBr$_2$-DMF catalyzed reaction conditions for α-glycosylation.

Figure 4:
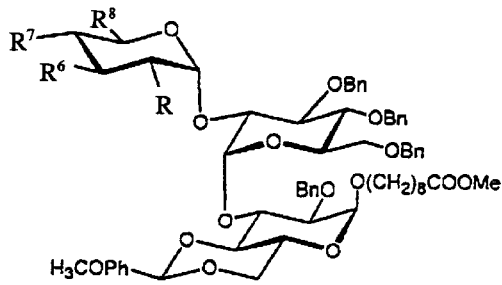
FIG. 4 illustrates various modified blocked and deblocked trisaccharide analogues useful in the synthesis of compounds of formula III.
Figure 4:
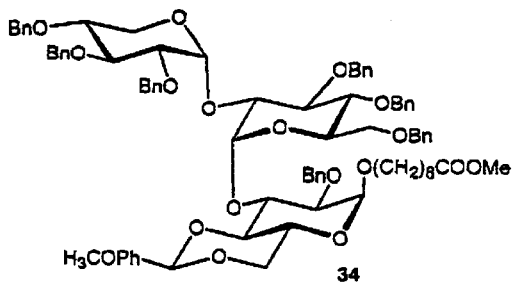
Figure 4:
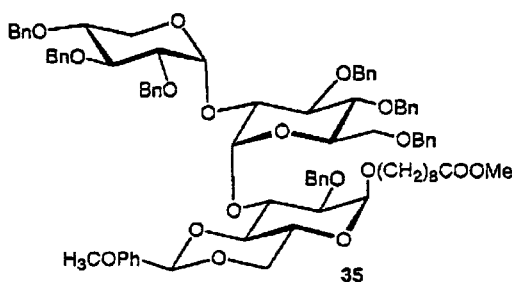
Figure 4:
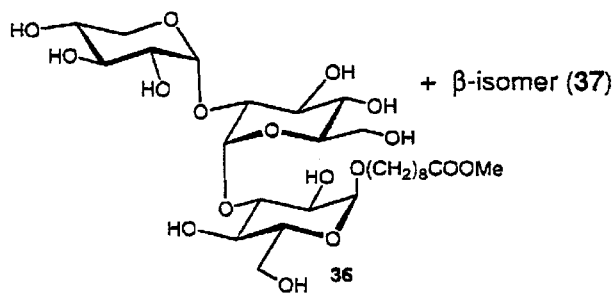
Figure 4:
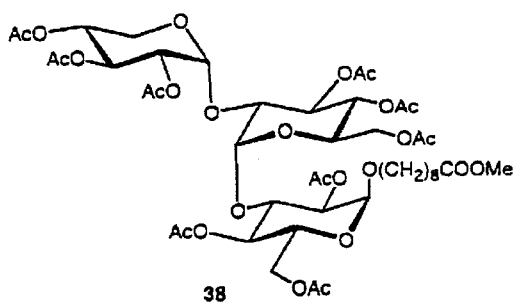
Figure 4:
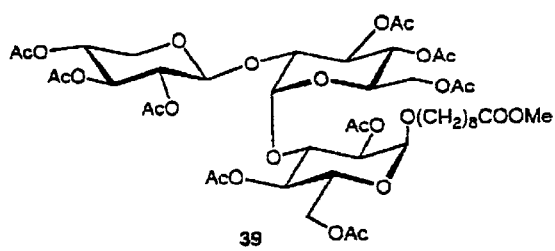
Figure 5:
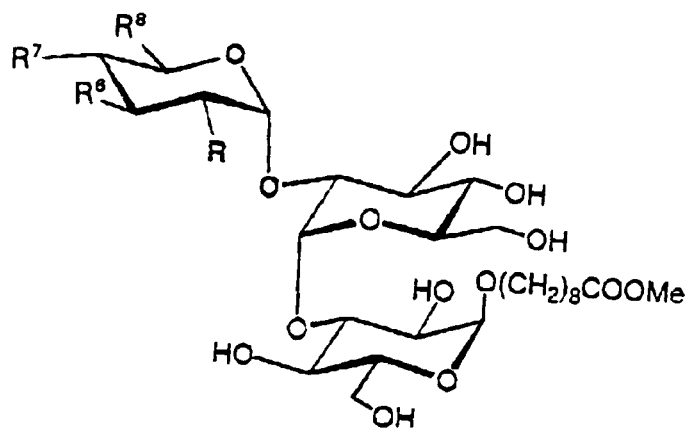
FIG. 5 illustrates compounds of this invention as well as 2" fluoro, deoxy, NH$_2$ and methoxy derivatives of α-D-Glcp-(1-2)-α-D-Glcp-(1-3)-α-D-Glcp which do not inhibit glucosidase I activity.

FIG. 4 illustrates the structures of protected trisaccharides prepared as below and in the examples. Specifically, alcohol 5 was reacted with glycosyl bromides 6, 8, 12, 13, 14, 15, 16 and 22 and thioglycosides 9, 10 and 21 to provide the modified blocked trisaccharides 23, 24, 28, 29, 30, 31, 32, 25, 33, 34 and 35 in yields of 71%, 23%, 71%, 73%, 70%, 69%, 73%, 72%, 70% and 77% respectively. However, glycosylation of 5 with 2-azido-3,4,6-tri-O-acetyl glucopyranosyl bromide was carried out with mercuric bromide, mercuric cyanide and drierite in dichloromethane which provided compound 26 in 64% yield.

The glycosylation reaction described above produced typically complex mixtures of products which required chromatographic purification on silica gel to produce the analytically pure materials described here. Iatrobeads were found to be a silica gel ideally suited to the chromatographic purification of such crude reaction products, as this silica gel proved to be the more powerful for separation, especially of (α:β) mixtures over other silica gels, e.g., silica gel-60 (230–400 mesh). However, compound 34 and 35 which exists as an α:β mixture could not be separated at the blocked stage.

Deprotection of 23, 24, 25, 28, 29, 30, 31, 32, 33, 34 and 35 was achieved by hydrogenation to provide the final deblocked products 40, 41, 42, 44, 45, 46, 47, 48, 49 and (36, 37 α+β) mixture in 89%, 84%, 91%, 85%, 94%, 81%, 81%, 89%, 81% and (90% α+β)yields. Compounds 36 and 37 could not be separated at this stage. Acetylation of 36 and 37 (α+β) provided 38 (68%) as a pure α-anomer.

Transesterification with sodium methoxide in methanol, followed by neutralization with resin, resin removal and solvent evaporation provided compound 34 in 79% yield. Compound 26 was O-deacetylated with sodium methoxide in methanol and hydrogenated over 5% pallium-on-carbon. Chromatography on BioGel P-2, and lyophilization gave the final product 43 in 86% yield.

Other modified trisaccharides can be prepared via conventional methods. For example, the synthesis of 4-methoxy analogues (the reducing sugar unit—the sugar bearing the —(CH$_2$)$_8$CO$_2$CH$_3$ aglycon) can be carried out from disaccharide intermediate 4 which is treated with sodium cyanoborohydride in the presence of ethereal HCl solution to provide 4-OH group available for modification. Treatment of 4-OH-disaccharide with sodium hydride in DMF using methyl iodide provides 4-OMe-disaccharide available. Deallylation as described earlier provides the 2'-OH group which is further extended as described herein.

Modified trisaccharides comprising deoxy, halo, amino modification in the glucose at the reducing terminus can also be prepared by conventional methods. For example, this synthesis can be carried out starting from 8-methoxycarbonyloctyl-2-O-benzyl-4,6-O-p-methoxy-O-benzylidene-galactopyranoside. Reaction of this intermediate with 2-O-allyl tetra-O-benzyl-glucopyranosyl bromide provides the disaccharide which may be reacted with 80% aqueous acetic acid or ceric ammonium nitrate to provide for the 4,6-diol. 6-position of this disaccharide may be blocked with benzyl protecting group and 4-OH may be reacted with DAST (diethylamino sulfur trifluoride) to provide 4F-disaccharide intermediate. 4-OH may also be transformed into 4-O-mesityl-derivative by reacting with mesityl chloride in pyridine which may be displaced with sodium azide and tetrabutyl ammonium chloride to provide azido and chloro substituents. Furthermore, 4F, 4-Cl and 4-azido disaccharide may be deallylated to provide 2'-OH-disaccharide for further synthesis. Reaction of this alcohol with tetrabenzyl glucosyl bromide may provide the protected trisaccharides which after hydrogenation with Pd/C may provide 4-Cl, 4-F and 4-NH$_2$ trisaccharides as a deblocked product. Furthermore, amino group may be transformed into a variety of substituents, like benzamide, nitrobenzamido, octamido and various amino acids may also be incorporated.

Still further, this invention includes compounds wherein the terminal glucose in the trisaccharide is replaced by valienamine, validamine, valiolamine, 5-deoxy-5-thioglucose, homonorijimycin, 1,5-trans-(C)-glucopyranosylamine. For example, trisaccharides wherein the terminal glucose is replaced by 1,5-trans(C)-glucopyranosyl residue are synthesized by using the disaccharide intermediate tetrabenzyl 1,5-trans(C) glucopyranosyl-1,6-anhydroglucose (described below) which may be treated with 2N-HCl solution to provide the opening of disaccharide. Acetylation followed by titanium tetrabromide reaction will provide disaccharide glycosyl donor to react with octyl-4,6-O-benzylidene-2-O-benzyl-α-D-glucopyranoside to provide (1-3) linked sugar by using AgOTf or AgClO$_4$ catalyst as promoter. The trisaccharide may be deprotected by deacetylation followed by hydrogenation to provide for the desired trisaccharide.

Trisaccharides wherein the terminal glucose is replaced by homonojirimycin (N-linked) can be prepared by using suitably protected disaccharide tri-O-benzyl-homonojirimycin-1,6-anhydroglucose (described below) which may be treated with 2N-HCl solution to provide opening of 1,6-anhydro-ring. Acetylation followed by titanium tetrabromide reaction may provide the bromide donor available for the reaction with octyl-4,6-O-benzylidene-2-O-benzyl-α-D-glucopyranoside as described above to give (1-3) linked sugar. Deprotection of this trisaccharide may be effected by sodium methoxide in methanol followed by hydrogenation with Pd/C to provide the required trisaccharide.

Trisaccharides wherein the terminal glucose is replaced by valienamine, validamine or valiolamine can be prepared by making use of valienamine-glucose, validamine-glucose and valiolamine-glucose the synthesis of which is described below as well as in U.S. patent application Ser. No. 08/466,621 filed on Jun. 6, 1995 as Attorney Docket No. 000475-048, now U.S. Pat. No. 5,571,796, and entitled "Administration of Valienamine-Related Disaccharide Compounds in Reducing Inflammation in a Sensitized Mammal Arising from Exposure to an Antigen" which application is incorporated herein by reference in its entirety. Specifically, acetylation of such compounds provides for the fully acetylated disaccharide which is then treated with titanium tetrabromide to provide the bromo disaccharides for coupling with octyl-4,6-O-benzylidene-2-O-benzyl-α-D-glucopyranoside. Deprotection involves deacetylation and hydrogenation to provide the three pseudo sugar trisaccharides.

Trisaccharides wherein the terminal glucose is replaced by 5-deoxy-5-thioglucose can be prepared by using the common intermediate 5 (2'-OH glycosyl acceptor) which is reacted with known 2,3,4,6-tetra-O-acetyl-5-deoxy-5-thio-α-D-glucopyranosyl)trichloroacetimidate to provide the protected trisaccharide in α,β mixture. Conventional deprotection involves deacetylation and hydrogenation to provide the desired trisaccharide.

Utility

The oligosaccharides of formula III possess glycosidase inhibition and, in particular, glycosidase I inhibition, and therefore are useful as anti-viral agents and in the treatment of diabetes mellitus and obesity. The anti-viral activity of these oligosaccharides are particular suited for the treatment of human immunodeficiency virus type 1, (HIV-1), where administration to a cell infected with this virus results in diminished production of infectious particles and reduces the cytopathic effects caused by this virus.

Such oligosaccharides are effective as anti-viral agents in mammals when administered at a dosage range of from about 0.5 mg to about 50 mg/kg of body weight, and preferably from about 5 to about 20 mg/kg of body weight. The specific dose employed is regulated by the particular virus being treated as well as by the judgment of the attending clinician depending upon factors such as the severity of the viral infection, the age and general condition of the patient, and the like.

The glycosidase inhibition properties of the oligosaccharides of formula III can also be employed in the dietary management of carbohydrate-dependent metabolic disorders such as diabetes, obesity, hyperglycemia and hyperlipemia by inhibiting in vivo the metabolism of carbohydrates and, when so used, are typically administered to the mammal at a dosage range of from about 0.50 mg to about 50 mg/kg of body weight, and preferably from about 5 to about 20 mg/kg of body weight. The specific dose employed is regulated by the particular condition being treated as well as by the judgment of the attending clinician depending upon factors such as the severity of the condition, the age and general condition of the patient, and the like.

Administration of these oligosaccharides to the mammalian patient is typically achieved by use of a pharmaceutical composition. Such pharmaceutical compositions are formulated for oral, parenteral, intranasal, intrapulmonary, transdermal and intravenous administration and comprise a pharmaceutically acceptable excipient and from about 1 to 95 weight percent of an oligosaccharide of formula III or a pharmaceutically acceptable salt thereof.

The glycosidase inhibitors of formula III can also be used for diagnostic/medicinal purposes to evaluate the pathology of viral infections. Specifically, the glycosidase inhibitors can be used to determined the effect of surface glycans on viral particles by interfering with normal glycan biosynthesis thereby presenting a viral particle having a structural defect in the surface glycans. The effect of the structural defect (e.g., on the ability of the viral particle to proliferate and/or to infect a target cell) can be evaluated.

Likewise, the glycosidase inhibitors of formula III, by virtue of their tight binding to the complementary glycosidases, can be used to recover such complementary glycosidases from a solution containing such glycosidases. For example, in one embodiment, the glycosidase inhibitor is covalently attached to a solid support via an aglycon linking arm (linker) and a solution comprising the complementary glycosidase is passed over the solid support thereby binding this glycosidase to the immobilized glycosidase inhibitor. See, for example, Bause et al.[46]

Oligosaccharides of formulas I and II define intermediates useful in the preparation of oligosaccharides of formula III.

The following examples are offered to illustrate this invention and are not to be construed in any way to limit the scope of the invention. Unless otherwise stated, all temperatures are in degrees Celsius. In the examples, unless otherwise noted, the abbreviations employed have their generally accepted meaning:

AIBN=azobisisobutyronitrile
ax=axial
bd=broad doublet
bs=broad singlet
d=doublet
dd=doublet of doublets
ddd=doublet of doublets of doublets
DMF=N,N-dimethylformamide
eq=equatorial
gem=indicates attachment to some atom
g=gram
h=hour
$^1$H-n.m.r.=proton nuclear magnetic resonance
Hz=Hertz
i.r.=infra red
kg=kilogram
L=liter
m=multiplet
M=molar
mg=milligram
mL=milliliter
mmol=millimol
N=Normal
q=quartet
s=singlet
t=triplet
THF=tetrahydrofuran
µL=microliter
µm=micron
Bro-Gel P2, P4 (200–400 mesh)
IRC-50 resin (H$^+$form)=ion exchange resin IR-C50 (H$^+$form) available from Rohm & Haas, Philadelphia, Pa.
Iatrobeads were obtained from Iatron Laboratories, Tokyo, Japan Examples 1–52 are synthetic examples illustrating the preparation of several compounds of the claimed invention. Example 53 is a biological example illustrating the glucosidase inhibition properties of the oligosaccharides of formula III.

EXAMPLES

Example 1

Synthesis of 8-Methoxycarbonyloctyl 2-O-benzyl-4, 6-O-p-methoxy-benzylidene-α-D-glucopyranoside (3)

Compound 2 (2.5 g, 5.81 mmol) was dissolved in acetonitrile (10 mL) and p-methoxy-benzaldehyde dimethyl acetal (2.5 mL) and p-toluene sulfonic acid (250 mg) were added. The reaction mixture was stirred for 1 h at room temperature and neutralized with triethylamine. Solvent was evaporated and the residue was purified by chromatography on silica gel using (hexane:ethyl acetate; 3:1) as eluant to provide 3 (2.3 g, 71%) as a solid; $[\alpha]_D$+45.22° (c 0.58, chloroform). $^1$H-n.m.r. (CDCl$_3$): δ 5.29(s, 1H, C$_6$H$_5$CHO$_2$), 4.74(d, 1H, J$_{1,2}$ 3.8 Hz, H-1), 4.71(ABq, 2H, J$_{gem}$ 12.0 Hz, C$_6$H$_5$CH$_2$), 3.79, 3.66(s, 3H each, OCH$_3$), 2.30(t, 2H, J 7.5 Hz, CH$_2$COO).

Example 2

Synthesis of 8-Methoxycarbonyloctyl 2-O-benzyl-4, 6-O-p-methoxy-benzylidene-3-O-(2-O-allyl-3,4,6-tri-O-benzyl-α-D-glucopyranosyl)-α-D-glucopyranoside (4)

To a mixture of compound 3 (2.1 g, 3.76 mmol) in dry dichloromethane (2 mL) containing tetraethylammonium bromide (1.1 g, 5.64 mmol), dry DMF (2.9 mL, 37.6 mmol) and molecular sieves (6.3 g) was added freshly prepared 2-O-allyl-3,4,6-tri-O-benzyl-α-D glucopyranosyl bromide 7 (10. 4 g, 18.8 mmol) and the reaction mixture was left stirring at room temperature for 72 h. Excess of bromide was decomposed by adding methanol (2 mL). The reaction mixture was filtered, evaporated and purified by chromatography on silica gel using (hexane: ethyl acetate; 3:1) as eluant. Pure 4 (3.5 g, 90.1%) was obtained as a syrup; $[\alpha]_D$+65.08° (c 0.32, chloroform). $^1$H-n.m.r. (CDCl$_3$): δ 5.63(m, 1H, CH$_2$—CH=CH$_2$), 5.46(s, 1H, C$_6$H$_5$CHO$_2$), 4.85(d, 1H, J$_{1',2'}$ 3.8 Hz, H-1'), 4.78(d, 1H, J$_{1,2}$ 3.5 Hz, H-1), 3.80, 3.65(s, 3H each, OCH$_3$), 2.30(t, 2H, J 7.5 Hz, CH$_2$COO).

Example 3

8-Methoxycarbonyloctyl 2-O-benzyl-4,6-O-p-methoxy-benzylidene-3-O-(3,4,6-tri-O-benzyl-α-D-glucopyranosyl)-α-D-glucopyranoside (5)

A solution of 4 (3.2 g, 3.1 mmol) tristriphenylphosphinerhodium (I) chloride (429.8 mg, 0.47 mmol), 1,4-diazabicyclo [2.2.2] octane (156.4 mg, 1.39 mmol) in ethanol-benzene-water (7:3:1, 100 mL) was refluxed for 24 h. The solvent was evaporated and the residue dissolved in acetone (100 mL) containing a trace amount of mercuric oxide (10 mg). To this solution was added a solution of mercuric chloride (3.0 g) in acetone-water (9:1, 50 mL), and the mixture was stirred at room temperature for 45 minutes. Following evaporation of the solvent, the residue was taken up in dichloromethane (250 mL). The dichloromethane solution was washed with 30% aqueous potassium bromide and water. The organic layer was dried (Na$_4$SO$_4$) and evaporated to give an oily residue that was purified by chromatography on silica gel using (hexane:ethyl acetate; 2:1) as eluant. The title compound was obtained as a white foam (2.5 g, 81.4%). $[\alpha]_D$ +44.85° (c 0.17, chloroform). $^1$H-n.m.r. (CDCl$_3$): δ 5.48(s, 1H, C$_6$H$_5$CHO$_2$), 5.28(d, 1H, J$_{1',2'}$3.2 Hz, H-1'), 4.74(d, 1H, J$_{1,2}$ 3.8 Hz, H-1), 3.69, 3.66(s, 3H each, OCH$_3$), 2.73(d, 1H, J 9.5 Hz, OH, D$_2$O exchangeable), 2.30(t, 2H, J 7.5 Hz, CH$_2$COO).

Example 4

Synthesis of 2,3,4,6-tetra-O-benzyl-α-D-glucopyranoside Bromide (6)

To a mixture of α-methyl glucopyanoside (21.6 g) and sodium hydride (30 g) in 700 mL of DMF (dried over molecular sieves) was added benzyl bromide (80 mL) dropwise at 0° C. After stirring for 50 hours at room temperature, an additional amount of sodium hydride (11.0 g) and benzyl bromide (25.0 mL) was added. Afterwards, the reaction mixture was diluted with dichloromethane (1 L). The organic phase was washed with water (5×1 L), dried over $Na_2SO_4$, concentrated and the resulting benzylated product was used in the next step without further purification.

The benzylated product was dissolved in 1 L of acetic acid containing 400 mL of 2N HCl and stirred for 15 hours at 80° C. 300 mL of cold water was added and the mixture cooled in an ice bath for 2 hours. Crystals were filtered, washed with 200 mL of aqueous acetic acid (50% v/v), 300 mL of ice water and with aqueous methanol (75% v/v) successively. The crystal were recrystallized from ether and hexane to provide for 50.0 g of tetrabenzyl glucose.

Tetrabenzyl glucose 3 (4.0 g) was dissolved in dry dichloromethane (34.0 mL) and dry DMF (2.0 mL) and oxalyl bromide were added dropwise (1.0 mL) and the resulting reaction mixture stirred for 5 hours at room temperature. The mixture was diluted with dichloromethane (250 mL), poured into ice water, washed with cold water (3×250 mL), dried over $Na_2SO_4$, filtered and evaporated to provide the title compound (6) quantitatively.

Example 5

Synthesis of 2-allyl-3,4,6-tri-O-benzyl-D-glucopyranosyl bromide (compound 7)

To 2-O-allyl-glucopyranosyl piperdine (24.5 g) dissolved in DMF (200 mL) was added sodium hydride (50% dispersion in oil, 15.0 g) and the resulting mixture stirred for 0.5 hours at 0° C. Benzyl bromide (30.0 mL) was added dropwise and the resulting solution stirred overnight at room temperature. The reaction mixture was poured into ice water (500 mL) and then stirred for 30 minutes. The aqueous phase was then extracted with dichloromethane (3×200 mL), dried over $Na_2SO_4$, filtered, concentrated to provide for N-(2,O-allyl-3,4,6-tri-O-benzyl-β-D-glucopyranosyl)-piperidine which was used in the next reaction. Yield was quantitative.

The piperidine compound (47.6 g) prepared as above was dissolved in acetone (200 mL) and distilled water (100 mL) and acetic acid (50.0 mL) were added and then the resulting mixture gently refluxed over 0.5 hours. The mixture was then cooled and evaporated to dryness. Crystallization was carried out from a mixture of ether and hexane to provide 2-O-allyl-3,4,6-tri-O-benzyl-glucopyranose. Yield was 24.3 g.

2-O-allyl-3,4,6-tri-O-benzyl-glucopyranose (4.0 g) was dissolved in dichloromethane (50.0 mL) and dry DMF (1.3 mL). Oxalyl bromide (1.3 mL) was added dropwise at 0° C. to the reaction mixture and the resulting solution was left stirring for 2 hours at 0° to 5° C. The solution was then poured into 250 mL of water and 100 mL of $CH_2Cl_2$. The organic layer was then washed (4×150 mL) with water, dried over $Na_2SO_4$, filtered, concentrated and coevaporated with toluene. The yield was quantitative. The product was made freshly prior to use.

Example 6

Synthesis of 2-deoxy-2-fluoro-3,4,6-tri-O-benzyl-glucopyranosyl bromide (8)

A solution of known methyl-2-deoxy-2-fluoro-3-O-benzyl-4,6-O-benzylidene-α-D-glucopyranoside (2.5 g) was dissolved in 80% aqueous acetic acid (100 mL) and the reaction mixture stirred for 15 hours at room temperature by which time all of the starting material was completely converted into diol. The solvent was evaporated and the residue coevaporated with the aid of toluene and then benzylated directly with sodium hydride (600 mg) and benzyl bromide (3.0 mL) in DMF (20.0 mL). The reaction mixture was diluted with dichloromethane (100 mL) and washed with water (2×100 mL), dried over sodium sulfate, filtered and evaporated to dryness. The residue was purified by chromatography on silica gel using hexane-ethyl acetate (5:1) as eluent to provide for methyl-2-deoxy-2-fluoro-3,4,6-tri-O-benzyl-α-D-glucopyranoside (2.2 g).

A solution of concentrated $H_2SO_4$ (30 μL) in acetic anhydride (2 mL) was added dropwise over a 5 minute period to a solution of methyl-2-deoxy-2-fluoro-3,4,6-tri-O-benzyl-α-D-glucopyranoside (1.7 g) in acetic anhydride (2.5 mL) and the reaction mixture was stirred for 3 hours at 0° C. The reaction mixture was diluted with dichloromethane (100 mL) and washed with a saturated solution of sodium bicarbonate (5×100 mL) and water (5×100 mL), dried over sodium sulfate, filtered and evaporated to dryness. Chromatography of the syrup using hexane-ethyl acetate (5:1) as eluent provide acetyl-2-deoxy-2-fluoro-3,4,6-tri-O-benzyl-glucopyranose (800 mg).

Acetyl-2-deoxy-2-fluoro-3,4,6-tri-O-benzyl-glucopyranose (750 mg) was dissolved in anhydrous DMF (7.5 mL). Hydrazine acetate (300 mg) was added and the reaction mixture was stirred for 3 hours at room temperature until most of the starting material was converted into product. The solution was diluted with dichloromethane (150 mL) and the organic layer was washed with water (3×150 mL), dried over sodium sulfate, filtered and evaporated. Chromatography of the material on silica gel using hexane-ethyl acetate (5:1) as eluent provided 2-deoxy-2-fluoro-3,4, 6-tri-O-benzyl glucopyranose (500 mg).

2-Deoxy-2-fluoro-3,4,6-tri-O-benzyl glucopyranose (450 mg) was dissolved in dichloromethane (5.0 mL) and dry DMF (180 μL) was added. The reaction solution was cooled to 0° C. and oxalyl bromide (102 μL) was added. The resulting solution was stirred for 3–5 hours at 0° to 5° C. The solution was then diluted with dichloromethane (50 mL) and washed with water (2×50 mL), dried over sodium sulfate, filtered and evaporated to obtain the title compound.

Examples 7 and 8

Synthesis of Benzyl 2-deoxy-3,4,6-tri-O-benzyl-1-thio-(α,β)-D-glucpyranoside (9) and (10)

To a solution of 2-deoxy-glucose tetraacetate obtained from acetylation of 2-deoxy-glucose (1.5 g, 4.5 mmol) in dry dichloromethane (10 mL) was added benzyl mercaptan (1.1 mL, 9.0 mmol). To this mixture was added boron trifluoride ethereate (1.67 mL, 13.5 mmol) in one portion. The reaction mixture was stirred for 5 hours at room temperature then quenched with saturated sodium hydrogen carbonate. After $CO_2$ evolution had ceased, the organic layer was separated and aqueous layer extracted with dichloromethane (2×100 mL). The combined organic extracts were dried ($Na_2SO_4$) and evaporated to dryness. Column chromatography of the residue using hexane-ethyl acetate (2:1) as eluent provided benzyl 2-deoxy-3,4,6-tri-O-acetyl-1-thio-(α,β)-D-glucopyranoside (1.49 g, 77.5%) as an α,β mixture. $^1$H NMR (CHCl$_3$): δ 5.25(bd, $J_{1,2}$4.0 Hz,H-1α),2.15–1.95 (6×Ac,α,β).

Benzyl 2-deoxy-3,4,6-tri-O-acetyl-1-thio-(α,β)-D-glucopyranoside (900 mg, 2.2 mmol) was O-deacetylated as described earlier to provide deacetylated product which was directly benzylated exactly as described earlier to provide compounds 9 and 10 (1.19 g, 90.5%) as a syrup after chromatographic purification using hexane-ethyl acetate (5:1) as eluent. $^1$H NMR (CHCl$_3$): δ 5.28(bd, $J_{1,2}$4.5 Hz,H-1α),4.88(d,$J_{1,2}$10.0 Hz,H-1β), 2.29–1.66(m,H-2α and H-2β).

Example 9

Synthesis of 2-deoxy-2-azido-3,4,6tri-O-acetyl-glucopyransoyl bromide (11)

The title compound was prepared via known methods, e.g., Lemieux, et al., Offenlengunschrift 2 816 340.

Example 10

Synthesis of 2-O-methyl-3,4,6-tri-O-benzyl-α-D-glucopyranosyl bromide (12)

To a solution of 2,3,4,6-tetra-O-acetyl-glucopyranosyl bromide (51.6 g) in dry $CH_2Cl_2$ (120 mL) was added dry allyl alcohol (120 mL), 2,6-utidine (37 mL) and tetraethylammonium bromide (50.4 g). The resulting solution was stirred for 5 hours at room temperature, 3 hours at 50° C. and 15 hours at 30° C. The reaction mixture was poured into water and extracted the dichloromethane. The water layer was washed with chloroform (2×1 L), dried over $Na_2SO_4$, filtered and concentrated.

The concentrate (50.0 g) prepared as above was deacetylated with sodium methoxide (0.5 N) in methanol (1 L). The reaction mixture was neutralized with IR-120 resin, filtered and evaporated. Benzylation of the deacetylated material was carried out directly with sodium hydride in DMF using benzyl bromide to provide for the benzylated product (70 g).

The benzylated product (1.7 g) prepared as above was dissolved in dichloromethane (20 mL) and trimethylsilyl triflate (279 μL) was added dropwise thereto. After 30 minutes, the reaction was complete. The reaction solution was filtered and washed with dichloromethane (100 mL) and then poured into 125 mL of ice water. The resulting solution was extracted with dichloromethane (3×50 mL) dried over sodium sulfate, filtered, evaporated to provide for 1.6 g of product.

The entire amount of this product was dissolved in dry methanol (20 mL) and a solution of 0.5 N sodium methoxide (10 mL) in methanol was added and the resulting solution stirred for 0.5 hours. Afterwards, the solution was neutralized with IR-120($H^+$) resin, washed with methanol (3×30 mL), evaporated and the resulting material used directly for preparation of 2-O-methylation. Specifically, the product (1.32 g) was dissolved in dry DMF (10 mL) and sodium hydride (130 mg) was added followed by addition of methyl iodide (340 μL) at 0° C. The resulting solution was stirred for 1 hour at room temperature. At this time, the solution was diluted with dichloromethane (125 mL) and poured in an ice cold water solution and then extracted with $CH_2Cl_2$ (3×75 mL) dried ($Na_2SO_4$) and evaporated. Chromatography of the material using hexane-ethyl acetate (3:1) as eluent provided allyl-2-O-methyl-3,4,6-tri-O-benzyl-α-D-glucopyranoside (906 mg).

Allyl-2-O-methyl-3,4,6-tri-O-benzyl-α-D-glucopyranoside (850 mg) was deallylated by conventional methods using tris triphenylphosphine rhodium (I) chloride (120 mg), 1,4-diazabicyclo[2.2.2]octane (43 mg) and refluxing the mixture in ethanol-benzene-water (7:3:1) (20 mL). Hydrolysis was carried out by using mercuric chloride (600 mg) in acetone-water (9:1) (50 mL) mixture. Following evaporation of the solvent, compound was taken in $CH_2Cl_2$ (100 mL) and washed with 30% aqueous potassium bromide (2×100 mL) and water (2×100 mL), dried over $Na_2SO_4$ and evaporated to give an oily residue which was purified by chromatography on silica gel using hexane-ethyl acetate (3:1) as eluent to give 2-O-methyl-3,4,6-tri-O-benzyl-glucopyranoside (550 mg).

2-O-methyl-3,4,6-tri-O-benzyl-glucopyranoside (500 mg) was dissolved in dichloromethane (10.0 mL) and DMF (200 μL) was added. Oxalyl bromide (300 μL) was dropwise added over 15 minutes and the resulting mixture stirred for 2 hours at 0° to 5° C. The resulting solution was poured into 100 mL of water and 100 mL of $CH_2Cl_2$. The organic layer was washed with water (2×200 mL) dried over $Na_2SO_4$ and evaporated to provide the title compound. The yield was for this last step quantitative and synthesis was conducted just prior to use.

Example 11

Synthesis of 3-deoxy-2,4,6-tri-O-benzyl-glucopyranosyl bromide (13)

Known 1,2,4,6-tetra-O-acetyl-3-O-benzylglucopyranose (10.0 g) was hydrogenated with palladium on carbon (5.0 g) in methanol (100 mL) by stirring the reaction mixture for 1 hour at room temperature and atmospheric pressure to provide for 1,2,4,6-tetra-O-acetyl-glucopyranoside (6 g).

1,2,4,6-tetra-O-acetyl-glucopyranoside (6 g) was dissolved in anhydrous acetonitrile (120 mL) and dimethylaminopyridine (3.6 g) and phenyl-chlorothionoformate (5.4 mL) was added thereto. The resulting solution was refluxed. After complete disappearance of the starting material, the reaction mixture was diluted with dichloromethane (250 mL) and washed with water (2×250 mL), dried over $Na_2SO_4$, evaporated and purified by chromatography on silica gel using hexane-ethyl acetate (3:2) as eluent to provide for 1,2,4,6-tetra-O-acetyl-3-O-phenylthiono-glucopyranose (5.2 g).

1,2,4,6-tetra-O-acetyl-3-O-phenylthiono-glucopyranose (5.2 g) was dissolved in toluene (50 mL) and added to tributyl tin hydride (6.7 mL) and azobisisobutryonitrile (AIBN) (2.8 g). The reaction mixture was heated for 1 to 3 hours at 80° C. to provide for 3-deoxy-2,4,6-tri-O-acetyl-glucopyranose (4.5 g).

3-deoxy-2,4,6-tri-O-acetyl-glucopyranose (4.5 g) was dissolved in freshly distilled mixture of dichloromethane-ethyl acetate (9:1) (15.0 mL). Titanium tetrabromide (7.5 g) was added slowly at 0° C. and the reaction mixture was allowed to stir at room temperature for 15 hours. The reaction solution was then diluted with methylene chloride (250 mL) and sodium acetate was added. The organic layer was washed with water (3×250 mL), dried over $Na_2SO_4$, filtered and evaporated to give the bromide quantitatively.

A mixture of 3-deoxy-2,4,6-tri-O-acetyl-α-D-glucopyranosyl bromide (4.5 g), molecular sieves (4.5 g), silver carbonate (4.5 g), dichloromethane (20.0 mL) and allyl alcohol (4.5 mL) was stirred in the dark at room temperature for 12 hours. The precipitate was washed with dichloromethane and combined filtrate and washings were concentrated to a syrup. Chromatography of the material on silica gel using hexane-ethyl acetate (3:1) and (2:1) as eluent provided allyl-3-deoxy-2,4,6-tri-O-acetyl-β-D-glucopyranoside (3.5 g).

Allyl-3-deoxy-2,4,6-tri-O-acetyl-β-D-glucopyranoside (3 g) was dissolved in methanol (20 mL) and a catalytic amount of sodium methoxide (0.5 m in methanol) was added. The reaction solution was stirred for 5 hours at room temperature. The reaction mixture was neutralized with IR-120($H^+$) resin, filtered, evaporated and benzylated with benzyl bromide (2.5 mL), sodium hydride (3.0 g) in DMF (20.0 mL) to provide for allyl-3-deoxy-2,4,6-tri-O-benzyl-β-D-glucopyranoside (4.0 g) after purification of the compound by chromatography on silica gel using hexane-ethyl acetate (5:1) as eluent.

Allyl-3-deoxy-2,4,6-tri-O-benzyl-β-D-glucopyranoside (3.5 g) was dissolved in a mixture of ethanol-benzene-water (7:3:1, 70 mL) and tris triphenylphosphine rhodium (I) chloride (500 mg) and 1,4-diazabicyclo[2.2.2]octane (216 mg) was added thereto. The reaction mixture was refluxed for 5 hours and taken to dryness. The isomerized product was hydrolyzed by dissolving the compound in a mixture of acetone-water (9:1, 100 mL) and adding mercury (II) chloride (18.0 g) and mercury (II) oxide (170 g). Stirred the reaction mixture for 30–45 minutes at room temperature. Filtered, evaporated and redissolved the residue in dichloromethane (150 mL) and washed successively with 30% KBr solution (2×150 mL) and water (2×150 mL), dried over sodium sulfate, filtered and evaporated to dryness. The syrup was purified by chromatography on silica gel using hexane-ethyl acetate (5:1) as eluent to give 3-deoxy-2,4,6-tri-O-benzyl-glucopyranose (2.5 g).

3-Deoxy-2,4,6-tri-O-benzyl-glucopyranose (2.2 g) was dissolved in dichloromethane (20 mL) and dry DMF (880 µL) was added. The reaction solution was cooled at 0° C. and oxalyl bromide (500 µL) was added and the resulting solution stirred at 0° to 5° C. for 1 hour. The solution was then diluted with dichloromethane (100 mL) and washed with water (3×100 mL), dried over sodium sulfate, filtered and evaporated to dryness to obtain 3-deoxy-2,4,6-tri-O-benzyl-glucopyranosyl bromide (compound 13).

Example 12

Synthesis of 3-O-methyl-2,4,6-tri-O-benzyl-glucopyranosylbromide (14)

Diacetone glucose (20 g), DMF (200 mL) and sodium hydride (2.78 g) were combined and then stirred for 20 minutes at 0° C. Methyl iodide (7.2 mL) was then dropwise added to the solution which was then stirred for 2 hours at room temperature. The reaction mixture was then diluted with $CH_2Cl_2$ (1 L) and washed with water (3×1 L), filtered, dried over sodium sulfate and evaporated which gave quantitative yield of 3-O-methyl-1,2:5,6-di-O-isopropylidine-glucopyranose (18.0 g) which was used without further purification.

3-O-methyl-1,2:5,6-di-O-isopropylidine-glucopyranose (10.2 g) was dissolved in 90% aqueous trifluoroacetic acid (30 mL) and stirred for 1 hour at room temperature. The reaction mixture was evaporated and then coevaporated with toluene followed by ethanol coevaporation to provide the product which was directly used for further allyl glycosylation. 7.9 g of 3-O-methyl-glucopyranose was dissolved in 50 mL of dry allyl alcohol and 120 µL of trifluoromethanesulfonic acid was added. The mixture was heated for 5½ h at 80° C. Triethylamine (1 mL) was added to destroy excess trifluoromethanesulfonic acid, evaporated and coevaporated with water to remove allyl alcohol. The material was purified by chromatography on silica gel using dichloromethane-methanol (20:1) as eluent to yield allyl-3-O-methyl-glucopyranose (4.85 g, 50.8%).

Allyl-3-O-methyl-glucopyranose (4.5 g) was dissolved in anhydrous DMF (120 mL) and sodium hydride (1.84 g, 50% dispersion in oil) was added thereto. The resulting solution was stirred for 0.5 hours at 0° C. Benzyl bromide (6.8 mL) was added dropwise at 0° to 5° C. and the reaction mixture was then stirred for 4 hours at room temperature. The reaction mixture was quenched by adding methanol, diluted with dichloromethane (250 mL) and washed with water (3×250 mL), dried over $Na_2SO_4$, filtered and evaporated. The material was purified by chromatography on silica gel using hexane-ethyl acetate (5:1) as eluent. The evaporated fractions from column were crystallized from a mixture of dichloromethane and hexane to provide for allyl-3-O-methyl-2,4,6-tri-O-benzyl-glucopyranose (8 g).

Allyl-3-O-methyl-2,4,6-tri-O-benzyl-glucopyranose (7.4 g) was refluxed for 5 hours in a mixture of ethanol/benzene/water (7:3:1) (500 mL) containing tris triphenylphosphine rhodium (I) chloride (1.05 g) and diazabicyclo[2.2.2]octane (445 mg). The isomerized product was hydrolyzed in acetone-water (9:1) (140 mL) using mercuric chloride (18.6 g) and mercuric oxide (383 mg) by stirring the reaction mixture at room temperature for 1 hour. The resulting solution was evaporated to dryness, diluted with methylene chloride (500 mL), filtered and washed with 30% KBr (3×500 mL) and water (3×500 mL), dried over $Na_2SO_4$, concentrated and purified by chromatography on silica gel using hexane-ethyl acetate (4:1) and (3:1) as eluents to provide 2,4,6-tri-O-benzyl-3-O-methyl-D-glucopyranose (5.0 g).

2,4,6-Tri-O-benzyl-3-O-methyl-D-glucopyranose (1.0 g) was dissolved in dry dichloromethane (10 mL) and DMF (500 µL) and oxalyl bromide were then dropwise (250 µL) added. The resulting reaction mixture was stirred for 1 hour at 0° to 5° C. and for 1 hour at room temperature. The reaction mixture was then diluted with dichloromethane (250 mL) and washed with water (3×250 mL) to provide for the title compound quantitatively for this last step.

Example 13

Synthesis of 4deoxy-2,3,6-tri-O-benzyl-glucopyranosyl bromide (15)

Allyl-2,3,6-tri-O-benzyl-glucopyranose (as per Example 14) (960 mg) was dissolved in dry pyridine and added 65 µL of sulfuryl chloride at 0° C. dropwise. The reaction mixture was stirred at this temperature for 15 hours. Dichloromethane (150 mL) was added and the resulting solution was washed with sodium bicarbonate (2×150 mL) and water (2×150 mL). Solvent removal left the residue which was purified by chromatography on silica gel using hexane-ethyl acetate (5:1) as eluent to provide compound allyl 4-chloro-4-deoxy-2,3,6-tri-O-benzyl-galactopyranose (550 mg).

A mixture of allyl 4-chloro-4-deoxy-2,3,6-tri-O-benzyl-galactopyranose (500 mg), of tributyltin hydride (2 eq) and AIBN (1.0 eq) in 20 mL toluene was heated at 90° C. for 3 hours. Solvent was evaporated and the residue was chromatographed on a silica gel column using hexane-ethyl acetate (5:1) as eluent to provide allyl-4-deoxy-2,3,6-tri-O-benzyl-glucopyranoside (300 mg).

Allyl-4-deoxy-2,3,6-tri-O-benzyl-glucopyranoside (2.46 g) was first benzylated with benzyl bromide and sodium hydride and then dissolved in a mixture of ethanol-benzene and water (7:3:1, 50 mL) and tris triphenylphosphine rhodium (I) chloride (350 mg) and 1,4-diazabicyclo[2.2.2] octane (148 mg) were added thereto. The resulting solution was refluxed for 5 hours. Afterwards, the solvent was evaporated to complete dryness and the isomerized product was hydrolyzed by dissolving it into a mixture of acetone-water (9:1, 50 mL) by adding mercuric chloride (5.6 g) followed by mercuric oxide (100 mg) and stirring the reaction mixture for 45 minutes at room temperature. Solvent was evaporated and dichloromethane (150 mL) was added. The dichloromethane layer was washed successively with 30% aqueous potassium bromide (2×150 mL) and water (2×50 mL), dried over $Na_2SO_4$, filtered and evaporated to dryness. The product was purified by chromatography on silica gel using hexane-ethyl acetate (5:1) as eluent to provide 4-deoxy-2,3,6-tri-O-benzyl-glucopyranoside (1.50 g).

4-Deoxy-2,3,6-tri-O-benzyl-glucopyranoside (1.5 g) was dissolved in dry dichloromethane (15.0 mL) and dry DMF (750 μL) was added. The reaction mixture was cooled to 0° C. and oxalyl bromide (350 μL) was dropwise added. The resulting solution was stirred it at 0° C. to 5° C. for 1 hour. The solution was then diluted with dichloromethane (100 mL), washed with water (2×100 mL), dried over sodium sulfate, filtered and evaporated to provide for the title compound. The yield was quantitative and ready to use.

Example 14

Synthesis of 4-O-methyl-2,3-6-tri-O-benzyl-glucopyranosyl bromide (16)

Compound 1 (obtained by reacting glucose in dry allyl alcohol in the presence of trifluoromethane sulfonic acid and refluxing for 6 hours at 80° C.) (27.9 g) was dissolved in anhydrous DMF (250 mL) and added p-toluene sulfonic acid (1.46 g). Benzaldehyde dimethylacetyl (28.5 mL) was added to the reaction mixture and the resulting solution stirred for 7.5 hours at room temperature. Another 20.5 mL of benzyl-dehyde dimethylacetal was then added and this solution stirred for 15 hours at room temperature. The reaction mixture was neutralized with triethylamine, evaporated to dryness, coevaporated with water. Diluted with 300 mL of $CH_2Cl_2$ and washed with water (2×300 mL) dried over $Na_2SO_4$, filtered and evaporated to obtain allyl-4,6-O-benzylidene glucopyranose (35.3 g).

Allyl-4,6-O-benzylidene glucopyranose (2.86 g) was dissolved in anhydrous DMF (100 mL). Sodium hydride (50% dispersion in oil) (669 mg) was added at 0° C. and dropwise addition of benzyl bromide (2.77 mL) was made at 0° C. The resulting solution was stirred for 4 hours at room temperature and then diluted with dichloromethane (250 mL), washed with water (2×250 mL), dried over $Na_2SO_4$, filtered and evaporated. The material was purified by chromatography on silica gel using hexane-ethyl acetate (3:1) and eluent to provide for allyl-2,3-di-O-benzyl-4,6-O-benzylidene glucopyranose (3.5 g).

Allyl-2,3-di-O-benzyl-4,6-O-benzylidene glucopyranose (8.0 g) was dissolved in anhydrous THF (250 mL) and added to it molecular sieves (8.0 g), methyl orange crystals and sodium cyanoborohydride (13.8 g). Dropwise addition of saturated HCl ethereal solution was made at 0° C. until the reaction mixture attains pH 3 at 0° C. After 15 minutes, the reaction was complete. Diluted with dichloromethane (500 mL) and filtered the solid mass and washed. The filtrate and washings were combined together and washed with sodium hydrogen carbonate (2×750 mL) and water (2×750 mL) before evaporation to a syrup. The compound was purified by chromatography using hexane-ethyl acetate (4:1) as eluent to give allyl-2,3,6-tri-O-benzyl-glucopyranose (5.5 g, 67.6%).

Allyl-2,3,6-tri-O-benzyl-glucopyranose (5.5 g) was dissolved in anhydrous DMF (50 mL) and sodium hydride (528 mg) (50% dispersion in oil) was added at 0° C. The reaction mixture was then stirred for 0.5 hours at 0° C. Methyl iodide (1.37 mL) was added dropwise at this temperature and the mixture was stirred for 1 hour at 0° to 5° C. The reaction solution was diluted with dichloromethane (100 mL) and washed with water (2×100 mL), dried over $Na_2SO_4$, filtered and evaporated to yield (5.72 g) of the product allyl-4-O-methyl-2,3,6,-tri-O-benzyl-glucopyranose.

Allyl-4-O-methyl-2,3,6,-tri-O-benzyl-glucopyranose (5.7 g) was dissolved in a mixture of ethanol-benzene-water (7:3:1; 75 mL). Tritriphenyl phosphine rhodium (I) chloride (805 mg) and 1,4-diazabicyclo[2₀2₀2]octane (342 mg) were added and the resulting solution refluxed for 5 hours. The solution was evaporated to dryness and the product was treated with mercury (II) chloride (14.4 g) and a trace of mercuric oxide (0.3 g) in a mixture of acetone and water (9:1, 50 mL). After 1 hour, reaction was complete. The reaction mixture was filtered, evaporated and dissolved in dichloromethane (250 mL). The organic solution was washed with 30% KBr solution (2×250 mL) and with water (2×250 mL), dried over sodium sulfate and purified by chromatography on silica gel using hexane-ethyl acetate (3:1) as eluent to provide 4-O-methyl-2,3-6-tri-O-benzyl-glucopyranose (2.32 g).

4-O-methyl-2,3-6-tri-O-benzyl-glucopyranose (1.5 g) was converted into its bromo derivative as described earlier with oxalyl bromide and DMF to provide the quantitative yield of the title compound.

Examples 15 and 16

Synthesis of 6-deoxy-glucose tetraacetate (17 and 18)

The title compounds were prepared by tritylation of glucose followed by acetylation and removal of the trityl group. The 6-OH group was then converted to the 6-chloro-6-deoxy group by sulfuryl chloride. Deoxygenation by tributyltin hydride and AIBN provided the 6-deoxy glucose acetate as a mixture of 1-α and 1-β isomers (17 and 18).

Example 17

Synthesis of Benzyl-6-deoxy-2,3,4-tri-O-acetyl-1-thio-α-D-glucopyranoside (19)

To a solution of 6-deoxy-glucose tetraacetate 17, 18 (1.2 g, 3.61 mmol) in dry dichloromethane (10 mL) was added benzyl mercaptan (847.9 μL, 7.22 mmol). To this mixture was added boron trifluoride etherate (888.3 mL, 7.22 mmol) in one portion. The reaction mixture was then stirred for 5 hours at room temperature and afterwards quenched with saturated sodium hydrogen carbonate. After $CO_2$ evaluation had ceased, the organic layer was separated and the aqueous layer extracted with dichloromethane (2×100 mL). The combined organic extracts were dried ($Na_2SO_4$) and evaporated to dryness. Column chromatography on the residue using hexane-ethyl acetate (2:1) as eluent provided the title compound (1.1 g 76.9%) as a white solid. $^1$H NMR (CDCl$_3$): δ 4.29(d,1H, $J_{1,2}$ 9.5 Hz, H-1), 1.22(d,1H, J7.0 Hz, H-6).

Example 18

Synthesis of benzyl-6deoxy-1-thio-α-D-glucopyranoside (20)

Treatment of compound 19 (950 mg, 2.40 mmol) with methanolic sodium methoxide for 15 hours at room temperature resulted in complete deacetylation. Neutralization of the mixture with IRC-50 (H$^+$) resin, subsequent removal of the resin by filtration and evaporation left 20 as a white solid which was dried under high vacuum overnight.

Example 19

Synthesis of benzyl-6-deoxy-3,4,6-tri-O-benzyl-1-thio-α-D-glucopyranoside (21)

Compound 20 prepared in Example 18 above was benzylated with benzyl bromide (1.1 mL) and sodium hydride (274.7 mg, 50% dispersion in DMF (25 mL). Purification by chromatography on silica gel provided the title compound (1.19 g, 84.9%) as a white powder. $^1$H NMR (CDCl$_3$): δ 4.25(d,1H, $J_{1,2}$ 9.5 Hz, H-1), 3.55(t,1H, $J_{3,4}=J_{4,5}$, 9.5 Hz, H-3), 3.43 (4, 1H, H-4), 1.26(d, 1H, J7.0 Hz-H6).

Example 20

Synthesis of 2,3,4-tri-O-benzyl-xylopyranosyl bromide (22)

Xylopyranose (15.0 g) was dissolved in allyl alcohol (150 mL) and trifluoromethane sulfonic acid (235 μL) was dropwise added 0° C. The reaction was stirred at 0° C. for 15 minutes and then heated at 80° C. for 4 hours. The reaction solution was then neutralized with triethylamine and evaporated to dryness. Chromatography of the material of silica gel using dichloromethane-methanol (19:1) as eluent provided allyl-xylopyranose (14.9 g).

Allyl-xylopyranose (1.62 g) was benzylated with benzyl bromide and sodium hydride and the benzylated product dissolved in a mixture of ethanol-benzene-water (7:3:1) (34 mL) and tris triphenylphosphine rhodium (I) chloride (250 mg) and 1,4-diazabicyclo[2.2.2]octane (108 mg) were added. The resulting solution was then refluxed for 1 hour. The solvent was evaporated to dryness and the residue redissolved in a mixture of acetone-water (9:1, 40 mg) to which was added mercury (II) chloride (8.9 g) and mercury (II) oxide (86 mg). The solution was then stirred for 2 hours at room temperature. The solvent was evaporated and the residue dissolved in CH$_2$Cl$_2$ (250 mL) and washed successively with 30% aqueous KBr (2×250 mL) and water (2×250 mL) before evaporation to a syrup. Evaporated and crystallized from ether and hexane to provide crystals of 2,3,4-tri-O-benzyl-xylopyranose (2.0 g).

2,3,4-tri-O-benzyl-xylopyranose was dissolved in dry dichloromethane (50 mL) and dry DMF (3.0 mL) was added. The reaction mixture was cooled at 0° C. and added dropwise oxayl bromide (1.4 mL). The reaction mixture was stirred for 1 hour at 0° to 5° C. and then diluted with dichloromethane (250 mL), washed with water (2×250 mL), dried over Na$_2$SO$_4$, filtered and evaporated to provide the title compound. The yield was quantitative for this step.

Example 21

Synthesis of 8-methoxycarbonyloctyl 3-O-[2-O-(2, 3,4,6-tetra-O-benzyl-α-D-glucopyranosyl)-3,4,6-tri-O-benzyl-α-D-glucopyranosyl]-2-O-benzyl-4,6-O-p-methoxy-benzylidene-α-D-glucopyranoside (23)

DMF (140.6 μL, 1.82 mmol) and tetraethyl-ammonium bromide (38.2 mg, 0.18 mmol) were added to a suspension of cupric bromide (243.4 mg, 1.1 mmol) and molecular sieves 4A (600 mg). After stirring the dark green mixture for 0.5 h at room temperature, a solution of compound 5 (120 mg, 0.12 mmol) in dichloromethane (1 mL) and of bromide 6 (365.4 mg, 0.61 mmol) in dichloromethane (1 mL) was syringed in dropwise in about 0.5 h. After stirring the reaction mixture for 36 h, collidine (100 μL) was added, then diluted with dichloromethane (25 mL). The solids were filtered and washed with dichloromethane (50 mL). Filtrate and washings were evaporated to get a syrup which was purified by chromatography on Iatrobeads using (hexane:ethyl acetate; 3:1) as eluent. Pure 23 (130 mg, 70.9%) was obtained as a syrup. $^1$H-n.m.r. (CDCl$_3$): δ 5.68(d, 1H, $J_{1'',2''}$ 3.5 Hz, H-1"), 5.14(s, 1H, C$_6$H$_5$CHO$_2$), 4.77(d, 1H, $J_{1',2}$ 3.5Hz, H-1"), 3.65, 3.64(s, 3H each, 2×OCH$_3$), 2.29(t, 2H, J 7.5 Hz, CH$_2$COO).

Example 22

Synthesis of 8-methoxycarbonyloctyl 3-O-[2-O-(2-deoxy-2-fluoro-3,4,6-tri-O-benzyl-α-D-glucopyranosyl)-3,4,6-tri-O-benzyl-α-D-glucopyranosyl]-2-O-benzyl-4,6-O-p-methoxy-benzylidene-α-D-glucopyranoside (24)

Compound 5 (150 mg, 0.25 mmol) was glycosylated with bromide 8 (390 mg, 0.76 mmol) exactly as described for the preparation of 23 to provide 24 (50 mg, 23.3%) as a syrup after chromatographic purification on silica gel column using (hexane:ethyl acetate; 5:1) as eluent. $^1$H-n.m.r. (CDCl$_3$): δ 5.49(s, 1H, C$_6$H$_5$CHO$_2$), 4.93(d, 1H, $J_{1'',2''}$ 3.8 Hz, H-1"), 4.84(d, 1H, $J_{1',2'}$ 3.8 Hz, H-1'), 3.65, 3.67(s, 3H each, 2×OCH$_3$), 2.30(t, 2H, J 7.5 Hz, CH$_2$COO).

Example 23

8-Methoxycarbonyloctyl 3-O-[2-O-(2-deoxy-3,4,6-tri-O-benzyl-α-D-glucopyranosyl)-3,4,6-tri-O-benzyl-α-D-glucopyranosyl]-2-O-benzyl-4,6-O-p-methoxy-benzylidene-α-D-glucopyranoside (25)

To a stirred mixture of DMF (111.3 μL, 1.44 mmol), tetraethylammonium bromide (30.2 mg, 0.14 mmol), cupric bromide (192.7 mg, 0.86 mmol) and molecular sieves (500 mg) were added compound 5 (95 mg, 0.096 mmol) in dichloromethane (1 mL) and thioglycoside as an α,β mixture 9, 10 (310 mg, 0.48 mmol) and stirring was continued for 36 h at room temperature. Collidine was added and diluted with dichloromethane (25 mL). The solids were removed by filtration and washed with dichloromethane (50 mL). Filtrate and washings were evaporated to obtain a syrup which was purified by chromatography on Iatrobeads using (hexane:ethyl acetate; 3:1) as eluent. Pure 25 (94.5 mg, 70%) was obtained as a syrup; $^1$H-n.m.r. (CDCl$_3$): δ 5.43(d, 1H, $J_{1'',2''}$ 3.2 Hz, H-1"), 5.3(s, 1H, C$_6$H$_5$CHO$_2$), 4.92(d,1H, $J_{1',2'}$ 3.8 Hz, H-1'), 4.79(d, 1H, $J_{1,2}$ 3.8 Hz, H-1) 3.69, 3.66(s, 3H each, OCH$_3$), 2.30(t, 2H, J 7.5 Hz, CH$_2$COO).

Example 24

Synthesis of 8-methoxycarbonyloctyl 3-O-[2-O-(2-deoxy-2-azido-3,4,6-tri-O-acetyl-α-D-glucopyranosyl)-3,4,6tri-O-benzyl-α-D-glucopyranosyl]-2-O-benzyl-4,6-O-p-methoxy-benzylidene-α-D-glucopyranoside (26)

Compound 5 (125 mg, 0.13 mmol), mercuric cyanide (318.6 mg, 1.26 mmol), powdered drierite (500 mg) in dry dichloromethane (1 mL) was stirred at room temperature for 1 h. A solution of tri-O-acetyl-2-azido-2-deoxy-glucopyranosyl bromide 11 (149 mg, 0.38 mmol) in dry dichloromethane (2 mL) was added followed by mercuric bromide (22.7 mg, 0.063 mmol) and the solution was stirred at room temperature for 2 days. After dilution with dichloromethane (50 mL), it was washed with 30% aqueous potassium bromide and water. The organic layer was dried (Na$_2$SO$_4$) and evaporated to give an oily residue that was purified by chromatography on an Iatrobeads column using (hexane:ethyl acetate; 3:1) as eluent. The title compound was obtained as s syrup (105 mg, 63.8%); $^1$H-n.m.r. (CDCl$_3$): δ 5.50(d, 1H, $J_{1'',2''}$ 3.5 Hz, H-1"), 3.81, 3.66(s, 3H each, 2×OCH$_3$), 2.30(t, 2H, J 7.5 Hz, CH$_2$COO), 2.09, 1.97, 1.86(s, 3H each, 3×Ac).

Example 25

Synthesis of 8-methoxycarbonyloctyl 3-O-[2-O-(2-O-methyl-3,4,6-tri-O-benzyl-α-D-glucopyranosyl)-3,4,6-tri-O-benzyl-α-D-glucopyranosyl]-2-O-benzyl-4,6-O-p-methoxy-benzylidene-α-D-glucopyranoside (28)

Reaction of alcohol 5 (117 mg, 0.12 mmol) with bromide 12 (5 equiv.), as described for the preparation of 23 gave, after chromatographic purification on Iatrobeads (hexane:ethyl acetate; 3:1), trisaccharide 28 (120 mg, 70.7%) as a syrup; $^1$H-n.m.r. (CDCl$_3$): δ 5.63(d, 1H, $J_{1'',2''}$ 3.5 Hz, H-1''), 5.44(s, 1H, C$_6$H$_5$C$\underline{H}$O$_2$), 5.05(d, 1H, $J_{1',2'}$ 3.5 Hz, H-1'), 3.66, 3.63(s, 9H, 3×OCH$_3$), 2.29(t, 2H, J 7.5 Hz, CH$_2$COO).

Example 26

Synthesis of 8-methoxycarbonyloctyl 3-O-[2-O-(3-deoxy-2,4,6-tri-O-benzyl-α-D-glucopyranosyl)-3,4,6-tri-O-benzyl-α-D-glucopyranosyl]-2-O-benzyl-4,6-O-p-methoxy-benzylidene-α-D-glucopyranoside (29)

Reaction of alcohol 5 (135 mg, 0.14 mmol) with bromide 13 (5 equiv.), as described for the preparation of 23 gave, after chromatographic purification on Iatrobeads (hexane:ethyl acetate; 3:1), trisaccharide 29 (140 mg, 73%) as a syrup. $^1$H-n.m.r. (CDCl$_3$): δ 5.67(d, 1H, $J_{1'',2''}$ 3.2 Hz, H-1''), 5.17(s, 1H, C$_6$H$_5$C$\underline{H}$O$_2$), 4.99(d, 1H, $J_{1',2'}$ 3.8 Hz, H-1'), 3.69, 3.66(s, 3H each, OCH$_3$), 2.38(ddd, 1H, $J_{3a,3e}$ 12.0, $J_{3e,4}$ 4.5 Hz, $J_{3e,2}$ 5.0 Hz, H-3e), 2.29(t, 2H, J 7.5 Hz, CH$_2$COO), 2.02(ddd, 1H, $J_{3a,2}$ 11.5, $J_{3a,4}$ 11.0 Hz, H-3a).

Example 27

Synthesis of 8-methoxycarbonyloctyl 3-O-[2-O-(3-O-methyl-2,4,6-tri-O-benzyl-α-D-glucopyranosyl)-3,4,6-tri-O-benzyl-α-D-glucopyranosyl]-2-O-benzyl-4,6-O-p-methoxy-benzylidene-α-D-glucopyranoside (30)

Reaction of alcohol 5 (110 mg, 0.11 mmol) with bromide 14 (5 equiv.), as described for the preparation of 23 gave, after chromatographic purification on Iatrobeads (hexane:ethyl acetate; 3:1), trisaccharide 30 (112 mg, 70.2%) as a syrup. $^1$H-n.m.r. (CDCl$_3$): δ 5.56(d, 1H, $J_{1'',2''}$ 3.5 Hz, H-1''), 5.12(s, 1H, C$_6$H$_5$C$\underline{H}$O$_2$), 5.08(d, 1H, $J_{1',2'}$ 3.8 Hz, H-1'), 3.66, 3.65, 3.60(s, 3H each, 3×OCH$_3$), 2.28(t, 2H, J 7.5 Hz, CH$_2$COO).

Example 28

Synthesis of 8-methoxycarbonyloctyl 3-O-[2-O-(4-deoxy-2,3,6-tri-O-benzyl-α-D-glucopyranosyl)-3,4,6-tri-O-benzyl-α-D-glucopyranosyl]-2-O-benzyl-4,6-O-p-methoxy-benzylidene-α-D-glucopyranoside (31)

Reaction of alcohol 5 (118 mg, 0.12 mmol) with bromide 15 (5 equiv.), as described for the preparation of 23 gave, after chromatographic purification on Iatrobeads (hexane:ethyl acetate; 3:1), trisaccharide 31 (116 mg, 69.2%) as a syrup; [α]$_D$+41° (c 0.26, chloroform). $^1$H-n.m.r. (CDCl$_3$): δ 5.60(d, 1H, $J_{1'',2''}$ 3.5 Hz, H-1''), 5.23(d, 1H, $J_{1',2'}$ 3.5 Hz, H-1'), 5.10(s, 1H, C$_6$H$_5$C$\underline{H}$O$_2$), 3.72, 3.64, (s, 3H each, 2×OCH$_3$), 2.29(t, 2H, J 7.5 Hz, CH$_2$COO).

Example 29

Synthesis of 8-methoxycarbonyloctyl 3-O-[2-O-(4-O-methyl-2,3,6-tri-O-benzyl-α-D-glucopyranosyl)-3,4,6-tri-O-benzyl-α-D-glucopyranosyl]-2-O-benzyl-4,6-O-p-methoxy-benzylidene-α-D-glucopyranoside (32)

Reaction of alcohol 5 (85 mg, 0.086 mmol) with bromide 16 (5 equiv.), as described for the preparation of 23 gave, after chromatographic purification on Iatrobeads (hexane:ethyl acetate; 3:1), trisaccharide 32 (90 mg, 73%) as a syrup. $^1$H-n.m.r. (CDCl$_3$): δ 5.66(d, 1H, $J_{1'',2''}$ 3.8 Hz, H-1''), 5.12(s, 1H, C$_6$H$_5$C$\underline{H}$O$_2$), 5.10 (d, 1H, $J_{1',2'}$ 3.8 Hz, H-1'), 3.66, 3.64, 3.46(s, 3H each, 3×OCH$_3$), 2.28(t, 2H, J 7.5 Hz, CH$_2$COO).

Example 30

Synthesis of 8-Methoxycarbonyloctyl 3-O-[2-O-(6-deoxy-2,3,4-tri-O-benzyl-α-D-glucopyranosyl)-3,4,6-tri-O-benzyl-α-D-glucopyranosyl]-2-O-benzyl-4,6-O-p-methoxy-benzylidene-α-D-glucopyranoside (33)

Reaction of alcohol 5 (100 mg, 0.10 mmol) with thioglycoside 21 (5 equiv.), as described for the preparation of 23 gave, after chromatographic purification on Iatrobeads (hexane:ethyl acetate; 3:1), trisaccharide 33 (102 mg, 71.8%) as a syrup. $^1$H-n.m.r. (CDCl$_3$): δ 5.69(d, 1H, $J_{1'',2''}$ 3.5 Hz, H-1''), 5.17(s, 1H, C$_6$H$_5$C$\underline{H}$O$_2$), 5.13(d, 1H, $J_{1',2'}$ 3.5 Hz, H-1'), 3.79, 3.65(s, 3H each, 2×OCH$_3$), 2.29(t, 2H, J 7.5 Hz, CH$_2$COO).

Example 31

Synthesis of 8-methoxycarbonyloctyl 3-O-[2-O-(2,3,4-tri-O-benzyl-α,β-D-xylopyranosyl)-3,4,6-tri-O-benzyl-α-D-glucopyranosyl]-2-O-benzyl-4,6-O-p-methoxy-benzylidene-α-D-glucopyranoside (34,35)

Reaction of alcohol 5 (150 mg, 0.15 mmol) with bromide 22 (5 equiv.), as described for the preparation of 23 gave, after chromatographic purification on Iatrobeads (hexane:ethyl acetate; 3:1), trisaccharide 34, 35 (162 mg, 76.8%) as a syrup. $^1$H-n.m.r. (CDCl$_3$): δ 5.62(d, 1H, $J_{1'',2''}$ 3.5 Hz, H-1''), 5.28(s, 1H, C$_6$H$_5$C$\underline{H}$O$_2$), 3.77, 3.66(s, 3H each, 2×OCH$_3$), 2.29(t, 2H, J 7.5 Hz, CH$_2$COO).

Example 32

Synthesis of 8-methoxycarbonyloctyl 3-O-[2-O-(2,3,4-tri-O-acetyl-α,β-D-xylopyranosyl)-3,4,6-tri-O-acetyl-α-D-glucopyranosyl]-2,4,6-tri-O-acetyl-α-D-glucopyranoside (36,37)

Compound 34, 35 (150 mg, 0.11 mmol) was dissolved in 95% ethanol (5 mL) containing 5% palladium-on-carbon (50 mg) and stirred under one atmosphere of hydrogen for 15 h, by which time t.l.c. showed the complete disappearance of 34, 35 to give one major spot which was devoid of U.V. adsorption in t.l.c. Removal of the catalyst by filtration followed by evaporation and purification by passage through BioGel P-2 (200–400 mesh) (50×2.5 cm) using 10% ethanol as eluant provided 36, 37 (65.5 mg, 90%) as a white powder followed lyophilization. However (α,β) mixture could not get separated at this stage and acetylated with pyridine (2 mL) and acetic anhydride (2 mL) to obtain α-isomer 38 (75 mg, 68%). $^1$H-n.m.r. (CDCl$_3$): δ 38 5.60(d, 1H, $J_{1'',2''}$ 3.5 Hz, H-1''), 3.62(s, 3H each, OCH$_3$), 2.26(t, 2H, J 7.5 Hz, CH$_2$COO), 2.07, 2.06, 2.03, 2.01, 2.00, 1.98, 1.97, 1.96(s, 3H each, 9×Ac); and its β-isomer 39 (20 mg, 18.2%) after chromatographic purification on Iatrobeads using (hexane;ethyl acetate; 2:1) as eluant. β-isomer was not characterized.

Example 33

Synthesis of 8-methoxycarbonyloctyl 3-O-[2-O-(α-D-xylopyranosyl)-α-D-glucopyranosyl]-α-D-glucopyranoside (36)

Compound 38 (75 mg, 0.073 mmol) was dissolved in methanol (5 mL) containing a trace of sodium methoxide (~0.1 M) and stirred the reaction mixture for 15 h at room temperature. Neutralization with IRC-50 (H$^+$) resin, resin removal and solvent evaporation provided a white powder 36 (37.5 mg, 79.3%) after BioGel P-2 and lyophilization. $^1$H-n.m.r. (D$_2$O): δ 5.54(d, 1H, J$_{1'',2''}$ 3.5 Hz, H-1"), 5.10(d, 1H, J$_{1',2'}$ 3.5 Hz, H-1'), 4.90(d, 1H, J$_{1,2}$ 3.5 Hz, H-1), 3.68(s, 3H each, OCH$_3$), 2.38(t, 2H, J 7.5 Hz, CH$_2$COO).

Example 34

Synthesis of 8-methoxycarbonyloctyl 3-O-[2-O-(α-D-glucopyranosyl)-α-D-glucopyranosyl]-α-D-glucopyranoside (40)

Compound 23 (72 mg, 0.048 mmol) was hydrogenated as described for the preparation of 36. After BioGel P-2 chromatography and lyophilization, 40 was obtained as a white powder (28.5 mg, 88.8%). $^1$H-n.m.r. (D$_2$O): δ 5.54(d, 1H, J$_{1'',2''}$ 3.5 Hz, H-1"), 5.18(d, 1H, J$_{1',2'}$ 3.5 Hz, H-1'), 4.91(d, 1H, J$_{1,2}$ 3.5 Hz, H-1), 3.69(s, 3H, OCH$_3$), 2.39(t, 2H, J 7.5 Hz, CH$_2$COO).

Example 35

Synthesis of 8-methoxycarbonyloctyl 3-O-[2-O-(2-deoxy-2-fluoro-α-D-glucopyranosyl)-α-D-glucopyranosyl]-α-D-glucopyranoside (41)

Compound 24 (75 mg, 0.053 mmol) was hydrogenated as described for the preparation of 36. The product was obtained as a white powder (30 mg, 84.3%) followed lyophilization. $^1$H-n.m.r. (D$_2$O): δ 5.69(d, 1H, J$_{1'',2''}$ 3.5 Hz, H-1"), 5.41(d, 1H, J$_{1',2'}$ 3.5 Hz, H-1'), 4.90(d, 1H, J$_{1,2}$ 3.5 Hz, H-1), 3.68(s, 3H, OCH$_3$), 2.38(t, 2H, J 7.5 Hz, CH$_2$COO).

Example 36

Synthesis of 8-methoxycarbonyloctyl 3-O-[2-O-(2-deoxy-α-D-glucopyranosyl)-α-D-glucopyranosyl]-α-D-glucopyranoside (42)

Compound 25 (55 mg, 0.039 mmol) was hydrogenated as described for the preparation of 36. The product was obtained as a white powder (23.5 mg, 91.3%) followed lyophilization. $^1$H-n.m.r. (D$_2$O): δ 5.56(d, 1H, J$_{1',2'}$ 3.5 Hz, H-1'), 5.26(d, 1H, J$_{1'',2''}$ 3.5 Hz, H-1"), 4.90(d, 1H, J$_{1,2}$ 3.5 Hz, H-1), 3.68(s, 3H, OCH$_3$), 2.38(t, 2H, J 7.5 Hz, CH$_2$COO), 2.16(dd, J 5 and 12 Hz, H-2e), 1.74(ddd, H-2a).

Example 37

Synthesis of 8-methoxycarbonyloctyl 3-O-[2-O-(2-amino-2-deoxy-α-D-glucopyranosyl)-α-D-glucopyranosyl]-α-D-glucopyranoside (43)

Compound 26 (120 mg, 0.092 mmol) was treated with methanolic sodium methoxide for 5 h at room temperature. Neutralization of the mixture with IRC-50 (H$^+$) resin, subsequent removal of the resin by filtration and evaporation left 27 as an oil which was directly hydrogenated as described for the preparation of 36 to get 43 (52.5 mg, 84.5%) as a white powder. $^1$H-n.m.r. (D$_2$O): δ 5.47(d, 1H, J$_{1'',2''}$ 3.5 Hz, H-1"), 5.35(d, 1H, J$_{1',2'}$ 3.5 Hz, H-1'), 4.95(d, 1H, J$_{1,2}$ 3.5 Hz, H-1), 3.69(s, 3H, OCH$_3$), 2.43(t, 2H, J 7.5 Hz, CH$_2$COO).

Example 38

Synthesis of 8-methoxycarbonyloctyl 3-O-[2-O-(2-methyl-α-D-gluopyranosyl)-α-D-glucopyranosyl]-α-D-glucopyranoside (44)

Compound 28 (65 mg, 0.045 mmol) was deprotected as described for the preparation of 36. The product was obtained as a white powder (26.5 mg, 85.1%). $^1$H-n.m.r. (D$_2$O): δ 5.65(d, 1H, J$_{1'',2''}$ 3.5 Hz, H-1"), 5.35(d, 1H, J$_{1',2'}$ 3.5 Hz, H-1'), 4.90(d, 1H, J$_{1,2}$ 3.5 Hz, H-1), 3.67, 3.55(s, 3H, 2×OCH$_3$), 2.37(t, 2H, J 7.5 Hz, CH$_2$COO).

Example 39

Synthesis of 8-methoxycarbonyloctyl 3-O-[2-O-(3-deoxy-α-D-glucopyranosyl)-α-D-glucopyranosyl]-α-D-glucopyranoside (45)

Compound 29 (85 mg, 0.06 mmol) was hydrogenated as processed for the preparation of 36 to provide 45 (37.2 mg, 93.5%) after lyophilization. $^1$H-n.m.r. (D$_2$O): δ 5.49(d, 1H, J$_{1'',2''}$ 3.5 Hz, H-1"), 5.04(d, J$_{1',2'}$ 3.5 Hz, H-1'), 4.88(d, 1H, J$_{1,2}$ 3.5 Hz, H-1), 3.66(s, 3H, OCH$_3$), 2.36(t, 2H, J 7.5 Hz, CH$_2$COO), 2.16(ddd, 1H, J$_{3a,3e}$ 12.0 Hz, H$_{2,3e}$ 4.5 Hz, H-3e), 1.83(ddd, 1H, J 11.5 and 11.0 Hz, H-3a).

Example 40

Synthesis of 8-methoxycarbonyloctyl 3-O-[2-O-(3-O-methyl-α-D-glucopyranosyl)-α-D-glucopyranosyl]-α-D-glucopyranoside (46)

Compound 30 (50 mg, 0.035 mmol) was hydrogenated as described for the preparation of 36 to provide 46 (19.5 mg, 81.4%) after lyophilization. $^1$H-n.m.r. (D$_2$O): δ 5.56(d, 1H, J$_{1'',2''}$ 3.5 Hz, H-1"), 5.20(d, J$_{1',2'}$ 3.5 Hz, H-1'), 4.94(d, 1H, J$_{1,2}$ 3.5 Hz, H-1), 3.72, 3.66(s, 3H each, 2×OCH$_3$), 2.42(t, 2H, J 7.5 Hz, CH$_2$COO).

Example 41

Synthesis of 8-methoxycarbonyloctyl 3-O-[2-O-(4-deoxy-α-D-glucopyranosyl)-α-D-glucopyranosyl]-α-D-glucopyranoside (47)

Compound 31 (58 mg, 0.041 mmol) was hydrogenated as described for the preparation of 36 to provide 47 (22 mg, 81.1%) after lyophilization. $^1$H-n.m.r. (D$_2$O): δ 5.50(d, 1H, J$_{1'',2''}$ 3.5 Hz, H-1"), 5.18(d, J$_{1',2'}$ 3.5 Hz, H-1'), 4.88(d, 1H, J$_{1,2}$ 3.5 Hz, H-1), 3.66(s, 3H, OCH$_3$), 2.36(t, 2H, J 7.5 Hz, CH$_2$COO), 1,98(m, 1H, H-4e), 1.46(ddd, 1H, J$_{3,4}$=J$_{4,5}$ 12.0, J$_{4a,4e}$ 12.5, H-4a).

Example 42

Synthesis of 8-Methoxycarbonyloctyl 3-O-[2-O-(4-O-methyl-α-D-glucopyranosyl)-α-D-glucopyranosyl]-α-D-glucopyranoside (48)

Compound 32 (73 mg, 0.051 mmol) was hydrogenated as described for the preparation of 36 to provide 48 (30 mg, 88.7%) after lyophilization. $^1$H-n.m.r. (D$_2$O): δ 5.56(d, 1H, J$_{1'',2''}$ 3.5 Hz, H-1"), 5.19(d, J$_{1',2'}$ 3.5 Hz, H-1'), 4.95(d, 1H, J$_{1,2}$ 3.5 Hz, H-1), 3.73, 3.61(s, 3H each, 2×OCH$_3$), 2.42(t, 2H, J 7.5 Hz, CH$_2$COO).

Example 43

Synthesis of 8-Methoxycarbonyl 3-O-[2-O-(6deoxy-α-D-glucopyranosyl)-α-D-glucopyranosyl]-α-D-glucopyranoside (49)

Compound 33 (72.5 mg, 0.052 mmol) was hydrogenated as described for the preparation of 36 to provide 49 (27.3 mg, 80.5%) as a white powder. $^1$H-n.m.r. (D$_2$O): δ 5.50(d, 1H, J$_{1'',2''}$ 3.5 Hz, H-1"), 5.10(d, 1H, J$_{1',2'}$ 3.5 Hz, H-1'), 4.89(d, 1H, J$_{1,2}$ 3.5 Hz, H-1), 3.68(s,3H each, OCH$_3$), 2.38(t, 2H, J 7.5 Hz, CH$_2$COO), 1.24(d, 3H, J 6.5 Hz, H-6").

Example 44

Synthesis of Valienamine-1,6-anhydroglucose [1,6-anhydro-2-deoxy-2-[1D-(1N,2,4/3)-5-C-hydroxymethyl-2,3,4trihydroxy-5-cyclohexen-1-yl)amino]-β-D-glucopyranose]

Step A) Synthesis of 1,6-anhydro-4-O-benzyl-2-deoxy-2-[1D-(1N,2,4/3)-(2,3,4-tri-O-benzyl-5-C-benzyloxymethyl-2,3,4-trihydroxy-5-cyclohexen-1-yl)amino]-β-D-glucopyranose A solution of protected valienamine, (1R)-(1,2,4/3)-2,3,4-tribenzyl-5-benzyloxy-methylcyclohex-5-enylamine made according to the method of Ogawa et al. *J. Chem Soc. Perkin Trans* (1988) (1.41 g, 2.63 mmol) was combined with the protected epoxide, 1,6-anhydro-4-O-benzyl-2,3-epoxy-glucose, made according to the method set forth in Cerny et al., *J. Czechoslav. Chem. Commun* 39 (1974) (3.28 g, 14.0 mmol), in n-propanol (28 ml) and was heated at 90° C. for 4 days. Solvent was evaporated, then co-evaporated with toluene and the residue was chromatographed on a silica gel column using hexane:ethylacetate (2:1) as eluent to provide 1,6-anhydro-4-O-benzyl-2-deoxy-2-[1D-(1N,2,4/3)-(2,3,4-tri-O-benzyl-5-C-benzyloxymethyl-2,3,4-trihydroxy-5-cyclohexen-1-yl)amino]-β-D-glucopyranose (1.2 g, 59.2%).

Step B) Synthesis of 1,6-anhydro-3-4-di-O-acetyl-2-deoxy-2-[1D-(1N,2,4/3)-(2,3,4-tri-O-acetyl-5-C-acetoxymethyl-2,3,4-trihydroxy-5-cyclohexen-1-yl)amino]-β-D-glucopyranose 1.09 g (1.41 mmol) of 1,6-anhydro-4-O-benzyl-2-deoxy-2-[1D-(1N,2,4/3)-2,3,4-tri-O-benzyl-5-C-benzyloxymethyl-2,3,4-trihydroxy-5-cyclohexen-1-yl)amino]-β-D-glucopyranose was dissolved in THF (20 ml) and liquid ammonia (~100 ml) was added at −78° C. Sodium (0.42 g) was added and the reaction mixture was stirred for 30 minutes at this temperature. NH$_4$Cl(2 g) was then added and ammonia and THF were evaporated at room temperature. The residue was acetylated in pyridine (5 ml) and acetic anhydride (5 ml). Excess of acetic anhydride was quenched by the addition of methanol. The reaction mixture was evaporated and dissolved in dichloromethane (100 ml) and washed sequentially with 5% HCl solution (2×100 ml), saturated NaHCO$_3$ solution (2×100 ml) and water (2×100 ml) before evaporation to a syrup. The syrup was purified by chromatography on silica gel using toluene:ethyl acetate (3:1) as eluent to provide 1,6-anhydro-3-4-di-O-acetyl-2-deoxy-2-[1D-(1N,2,4/3)-(2,3,4-tri-O-acetyl-5-C-acetoxymethyl-2,3,4-trihydroxy-5-cyclohexen-1-yl)amino]-β-D-glucopyranose (613 mg, 75.8%).

Step C) Synthesis of Valienamine-1,6-anhydroglucose [1,6-anhydro-2-deoxy-2-[1D-(1N,2,4/3)-5-C-hydroxymethyl-2,3,4-trihydroxy-5-cyclohexen-1-yl)amino]-β-D-glucopyranose]

482 mg (0.843 mmol) of 1,6-anhydro-3,4-di-O-acetyl-2-deoxy-2-[1D-(1N,2,4/3)-(2,3,4-tri-O-acetyl-5-C-acetoxymethyl-2,3,4-trihydroxy-5-cyclohexen-1-yl)amino]-β-D-glucopyranose was dissolved in dry methanol (20 ml) and a methanolic solution of sodium methoxide (0.5N, 0.1 ml) was added. After 4 hours, solvent was evaporated and the residue was purified by passing through a column of sephadex using water:ethanol (1:1) as eluent to provide pure 1,6-anhydro-2-deoxy-2-[1D-(1N,2,4/3)-5-C-hydroxymethyl-2,3,4-trihydroxy-5-cyclohexen-1-yl)amino]-β-D-glucopyranose (249 mg, 92.5%) as white powder after lyophilization.

Example 45

Synthesis of Valienamine-glucose [2-deoxy-2-[1D-(1N,2,4/3)-(5-C-hydroxymethyl-2,3,4trihydroxy-5-cyclohexan-1-yl)amino]-D-glucopyranose hydrochloride]

1,6-anhydro-2-deoxy-2-[1D-(1N,2,4/3)-5-C-hydroxymethyl-2,3,4-trihydroxy-5-cyclohexan-1-yl)amino]-β-D-glucopyranose (152.5 mg, 0.47 mmol) was heated at 100° C. in 2N HCl solution for 4 days. Solvent was removed by co-evaporation with water and the residue was purified by chromatography on an iatrobeads column (Iatron Laboratories, Japan) using toluene:chloroform:methanol:water, (65:38:3) as eluent to provide 2-deoxy-2-[ID-(1N,2,4/3)-(5-C-hydroxymethyl-2,3,4-trihydroxy-5-cyclohexan-1-yl)amino]-D-glucopyranose hydrochloride after lyophilization (116 mg, 65%).

Example 46

Synthesis of Valiolamine-1,6-anhydroglucose [1,6-anhydro-2-deoxy-2[1D-(1,2,4,5/3)-(1-C-hydroxymethyl-1,2,3,4 tetra-hydroxy-cyclohexyl)amino]-β-D-glucopyranose Step A) Synthesis of 1,6-anhydro-4-O-benzyl-2-deoxy-2[1D-(1/2,3)-1,2-di-O-benzyl-(5-C-trityloxymethyl-1,2-dihydroxy-6-cyclohexanyl)-amino]-glucopyranose A solution of protected valienamine made according to the procedure set forth in Hayashida et al., *J. Carbohydrate Chemistry* 7(1):83–94 (1988) (150 mg, 0.26 mmol) and protected epoxide, 1,6-anhydro-4 -O-benzyl-2,3-epoxy-glucose (309.2 mg, 1.32 mmol), described above in n-propanol (5 ml) was heated at 90° C. for 10 days. Solvent was evaporated, then coevaporated with toluene and the residue was chromatographed on a silica gel column using hexane:ethyl acetate (2:1) as eluent to provide 1,6-anhydro-4-O-benzyl-2-deoxy-2[1D-(1/2,3)-1,2-di-O-benzyl-(5-C-trityloxymethyl-1,2-dihydroxy-6-cyclohexanyl)-amino]-glucopyranose (150 mg, 69.9%).

Step B) Synthesis of 1,6-anhydro-4-O-benzyl-2-deoxy-2[1D-(1,2,4,5/3)-3,4-di-O-benzyl-(1-C-trityloxymethyl-1,2,3,4-tetrahydroxy-cyclohexyl)-amino]-β-D-glucopyranose Osmium tetroxide (2.0 mg) was added to a solution of the compound produced in A) above (120 mg, 0.15 mmol) and trimethylamine-N-oxide (32.7 mg, 0.29 mmol) in t-butanol (5 ml) containing pyridine (0.25 ml); the mixture was stirred in argon atmosphere for 6 hours at 60° to 70° C., treated with a 20% aqueous solution of sodium hydrogen sulfite (1.0 ml) at room temperature, diluted with saturated brine (10.0 ml) and extracted with dichloromethane (3×20 ml). The extract was washed with water, dried and concentrated. The residue was purified by chromatography on silica gel hexane:ethyl acetate (3:1) as eluent to give 1,6-anhydro-4-O-benzyl-2-deoxy-2[1D-(1,2,4,5/3)-3,4-di-O-benzyl-(1-C-trityloxymethyl-1,2,3,4-tetrahydroxy-cyclohexyl)-amino]-β-D-glucopyranose (26 mg, 20.8%).

Step C) Synthesis of 1,6-anhydro-2-deoxy-2-[1D-(1,2,4,5/3)-(1-C-hydroxymethyl-1,2,3,4-tetrahydroxy-cyclohexyl)amino]-β-D-glucopyranose The compound prepared in B) above (20 mg, 0.024 mmol) was dissolved in methanol (5 ml) containing 0.1% hydrochloric acid. Pd(OH)$_2$ on carbon (50 mg) was added and the reaction mixture stirred at atmospheric pressure for 2 days to give 1,6-anhydro-2-deoxy-2-[1 D-(1,2,4,5/3)-(1-C-hydroxymethyl-1,2,3,4-tetrahydroxy-cyclohexyl)amino]-β-D-glucopyranose (7 mg, 89%).

Example 47

Alternate synthesis of Valiolamine-1,6-anhydroglucose [1,6-anhydro-2-deoxy-2-[1D-(1,2,4,5/3)-(5-C-hydroxymethyl-1,2,3,4-tetrahydroxy-cyclohexyl)-amino]-β-D-glucopyranose Step A) Synthesis of 1D-(1/2,3)-1,2-di-O-benzyl-3-(trichloroethylamino)-5-(trityloxymethyl)-6-cyclohexene-1,2-diol A solution of trichloroethylchloroformate (308 mg, 1.45 mmol) in dichloromethane (2 ml) was added dropwise at 0° C. to a solution of protected valienamine made according to the method of Hayashida et al., *J. Carbohydrate Chemistry* 7(1):83–94 (1988) (550 mg, 0.97 mmol) in pyridine (4 ml) and dichloromethane (5 ml). The mixture was stirred overnight at room temperature, diluted with water (20 ml), stirred for a further 2 hours and extracted with dichloromethane (20 ml×3). The extract was washed with 1 M hydrochloric acid, aqueous sodium hydrogencarbonate, and sodium chloride, dried and concentrated. The residue was chromatographed on silica gel using benzene:ethyl acetate (98:2) as eluent to provide 1D-(1/2,3)-1,2-di-O-benzyl-3-(trichloroethylamino)-5-(trityloxymethyl)-6-cyclohexene-1,2-diol (430 mg, 59.7%).

Step B) Synthesis of IL-(1,2,4,5/3)-3,4-di-O-benzyl-5-(trichloroethylamino)-1-C-(trityloxymethyl)-cyclohexane-1,2,3,4-tetrol Osmium tetroxide (3.0 mg, 0.01 mmol) was added to a solution of the compound produced in A) above (350 mg, 0.47 mmol) and trimethyl-amine-N-oxide made according to the method of Ray and Matteson *Tetrahedron Lett.* 21:449 (1980) (104.7 mg, 0.94 mmol) in t-butanol (10 ml) containing pyridine (0.5 ml). The mixture was stirred in argon atmosphere for 6 hours at 60–70° C., treated with 20% aqueous solution of sodium hydrogen sulfite (2 ml) at room temperature, diluted with saturated brine (20 ml) and extracted with dichloromethane (3×20 ml). The extract was washed with water, dried and concentrated. The residue was purified by chromatography on silica gel using benzene:ethyl acetate (96:4) as eluent to give a syrup of IL-(1,2,4,5/3)-3,4-di-O-benzyl-5-(trichloroethylamino)-1-C-(trityloxymethyl)-cyclohexane-1,2,3,4-tetrol (182 mg, 48.8%). Apparently, cis-dihydroxylation of the c—c double bond took place exclusively from the α-side, as no compound, which should have been produced by the attack from the opposite side was detected.

Step C) Synthesis of IL-(1,2,4,5/3)-2-O-acetyl-3,4-di-O-benzyl-5-(trichloroethylamino)-1-C-(trityloxymethyl)-cyclohexene-1,2,3,4-tetrol Acetic anhydride (2 ml) was added at 0° C. to a solution of the compound produced in B) above (60 mg, 0.20 mmol) in dichloromethane (5 ml) and pyridine (2 ml); the mixture was stirred overnight at room temperature diluted with water (10 ml), stirred for a further 2 hours and extracted with dichloromethane (3×20 ml). The extract was successfully washed with 1 M hydrochloric acid and brine and concentrated. The residue was purified by chromatography on silica gel using benzene:ethyl acetate (9:1) as eluent to provide IL-(1,2,4,5/3)-2-O-acetyl-3,4-di-O-benzyl-5-(trichloroethylamino)-1-C-(trityloxymethyl)-cyclohexene-1,2,3,4-tetrol (145 mg, 86%).

Step D) Synthesis of 1L-(1,2,4,5/3)-2-O-acetyl-3,4-di-O-benzyl-5-amino-1-C-(trityloxy-methyl)-cyclohexene-1,2,3,4-tetrol The compound produced in C) above (140 mg, 0.17 mmol) was treated with fresh zinc in 80% aqueous acid for 5–10 hours at room temperature until all the starting material was converted into product. The product was filtered, evaporated and the residue was purified by chromatography on silica gel using benzene:ethyl acetate (9:1) as eluent to provide 1L-(1,2,4,5/3)-2-O-acetyl-3,4-di-O-benzyl-5-amino-1-C-(trityloxymethyl)-cyclohexene-1,2,3,4-tetrol (88 mg, 80%).

Step E) Synthesis of 1,6-anhydro-4-O-benzyl-2-deoxy-2-[1D-(1,2,4,5/3)-2-O-acetyl-3,4-di-O-benzyl-(1-C-trityloxymethyl-1,2,3,4-tetrahydroxy-cyclohexyl)-amino]-glucopyranose A solution of the compound produced in D) above (80 mg, 0.12 mmol) and the protected epoxide, 1,6-anhydro-4-O-benzyl-2,3-epoxy-glucose, described above (146 mg, 0.61 mmol) in n-propanol (3 ml) was heated at 90° C. for 7 days. Solvent was evaporated, co-evaporated with toluene and the residue was chromatographed on a silica gel column using hexane:ethyl acetate (2:1) as eluent to provide 1,6-anhydro-4-O-benzyl-2-deoxy-2-[1D-(1,2,4,5/3)-2-O-acetyl-3,4-di-O-benzyl-(1-C-trityloxymethyl-1,2,3,4-tetrahydroxy-cyclohexyl)-amino]-glucopyranose (80 mg, 74%).

Step F) Synthesis of 1,6-anhydro-4-O-benzyl-2-[1D-(1,2,4,5/3)-3,4-di-O-benzyl-(1-C-trityloxymethyl-1,2,3,4-tetrahydroxy-cyclohexyl)-amino]-glucopyranose The compound prepared in E) above (75 mg, 0.084 mmol) was deacetylated by sodium methoxide in methanol (0.5 M solution) by stirring the reaction mixture for 3 hours at room temperature to give 1,6-anhydro-4-O-benzyl-2-[1D-(1,2,4,5/3)-3,4-di-O-benzyl-(1-C-trityloxymethyl-1,2,3,4-tetrahydroxy-cyclohexyl)-amino]-glucopyranose (63 mg, 88%).

Step G) Synthesis of 1,6-anhydro-2-deoxy-2-[1D-(1,2,4,5/3)-(1-C-hydroxymethyl-1,2,3,4-tetrahydroxy-cyclohexyl)-amino]-β-D-glucopyranose The compound prepared in F) above (50 mg, 0.06 mmol) was dissolved in methanol (5 ml) containing 0.1% hydrochloric acid. Pd(OH)$_2$ on carbon (50 mg) was added and the reaction mixture stirred at atmospheric pressure for 2 days to give 1,6-anhydro-2-deoxy-2-[1D-( 1,2,4,5/3)-(1-C-hydroxymethyl-1,2,3,4-tetrahydroxy-cyclohexyl)-amino]-β-D-glucopyranose (16.5 mg, 83.7%).

Example 48

Synthesis of Valiolamine-glucose 1,6-anhydro-2-deoxy-2-[1D-(1,2,4,5/3)-(1-C-hydroxymethyl-1,2,3,4-tetrahydroxy-cyclohexyl)-amino]-β-D-glucopyranose (20 mg, 0.059%) was heated at 100° C. in 2N HCl solution for 4 days. Solvent was removed by co-evaporation with water and the residue was purified by chromatography on an Iatrobeads column (Iatron Laboratories, Japan) using toluene:chloroform:methanol:water, (65:38:3) as eluent to provide valiolamine-glucose-hydrochloride after lyophilization (15 mg, 71.2%).

Example 49

Synthesis of Protected Validamine for the preparation of Validamine-1,6-anhydroglucose and validamine-glucose hydrochloride Step A) Synthesis of 1L(1,3/2,4)-1-O-Acetyl-2,3,4-tri-O-benzyl-5-C-benzyloxymethyl-5-cyclohexene-1,2,3,4-tetrol 1.21 g (2.47 mmol) of compound 18 (Paulson et al., *Liebigs Ann. Chem.* 125–131 (1987)) was dissolved in pyridine (3.0 ml). Benzyl bromide (0.60 ml) was added followed by silver oxide (0.96 g). After 20 hours and 48 hours, more silver oxide was added in 0.48 g and 0.8 g quantities respectively. After 3 days, methanol was added and the mixture was stirred for 1 hour. The organic salts were filtered off. The filtrate was diluted with dichloromethane and washed with saturated sodium hydrogencarbonate solution and water, dried over $Na_2SO_4$ and evaporated. The syrup was purified by chromatography on silica gel using hexane:ethyl acetate (6:1) as eluent. Pure compound (852 mg, 84% based on consumption of the starting material) was obtained along with recovered starting material (347 mg).

Step B) Synthesis of 1L-(1,3,5/2,4)1-O-acetyl-5-C-benzyloxymethyl-2,3,4-tri-O-benzyl-1,2,3,4-cyclohexane tetrol and Pseudo-L-iodopyranose isomer 1L(1,3/2,4)-1-O-Acetyl-2,3,4-tri-O-benzyl-5-C-benzyloxymethyl-5-cyclohexene-1,2,3,4-tetrol (137.6 mg, 0.24 mmol) was dissolved in ethanol (4.0 ml) and $PtO_2$ catalyst was added (4 mg). The reaction mixture was stirred for 1 hour at room temperature and atmospheric pressure until most of the starting material was consumed. Chromatography of the material, after filtration of the catalyst on the pad of celite and evaporation, provided compound 1L-(1,3,5/2,4)1-O-acetyl-5-C-benzyloxymethyl-2,3,4-tri-O-benzyl-1,2,3,4-cyclohexane tetrol (70 mg, 50.6%) and its α-iodo isomer (60 mg, 43.5%). Chromatography was carried out twice: first using ethyl acetate: hexane (9:1) as eluent and the second time using carbon tetrachloride:hexane (4:1) as eluent.

Step C) Synthesis of 1L-(1,3,5/2,4)-5-C-benzyloxymethyl-2,3,4-tri-O-benzyl-1,2,3,4-cyclohexane tetrol 1L-(1,3,5/2,4)1-O-acetyl-5-C-benzyloxymethyl-2,3,4-tri-O-benzyl-1,2,3,4-cyclohexane tetrol (79 mg, 0.12 mmol) was dissolved in 5 ml of methanol and a catalytic amount of sodium methoxide in methanol (0.5 ml, 0.5N) was added to it. After stirring the reaction mixture for 1 hour at room temperature, it was neutralized by 1R-120-H+ (Amberlite) resin. The resulting compound was filtered from the resin and evaporated to dryness to obtain 1L-(1,3,5/2,4)-5-C-benzyloxymethyl-2,3,4-tri-O-benzyl-1,2,3,4-cyclohexane tetrol (55 mg, 85%).

Step D) Synthesis of 1D-(1,2,4/3,5)-1-azido-2,3,4-tri-O-benzyl-5-C-benzyloxymethyl-1,2,3,4-cyclohexane tetrol A benzene solution of hydrazoic acid (10%, 3.0 mL) was added to a mixture of 1L-(1,3,5/2,4)-5-C-benzyloxymethyl-2,3,4-tri-O-benzyl-1,2,3,4-cyclohexane tetrol (50 mg, 0.093 mmol) and triphenylphosphine (TPP) (97.4 mg, 0.37 mmol) in toluene (3.0 ml) and the whole mixture was thoroughly cooled. Diethylazodicarboxylate (DEAE) (0.1 ml) was added dropwise to the mixture, with stirring, at a temperature below $-10°$ and kept there for 30 minutes and for an additional 2 hours at room temperature. The precipitate was filtered off, and the filtrate was evaporated. The residue was chromatographed with benzene as the eluent, to provide 1D-(1,2,4/3,5)-1-azido-2,3,4-tri-O-benzyl-5-C-benzyloxymethyl-1,2,3,4-cyclohexane tetrol as a syrup (42 mg, 80.3%).

Step E) Synthesis of 1D-(1,2,4/3,5)-1-amino-2,3,4-tri-O-benzyl-5-C-benzyloxymethyl-1,2,3,4-cyclohexane tetrol Hydrogen sulfide was bubbled through a solution of 1D-(1,2,4/3,5)-1-azido-2,3,4-tri-O-benzyl-5-C-benzyloxymethyl-1,2,3,4-cyclohexane tetrol (40 mg, 0.071 mmol) in a mixture of pyridine (1 ml) and water (1.0 ml) for 2 hours at room temperature. The excess of $H_2O$ was removed by a stream of nitrogen. The reaction mixture was concentrated and the residue was purified on silica gel using benzene:ethyl acetate (9:1) as eluent to provide pure compound 1D-(1,2,4/3,5)-1-amino-2,3,4-tri-O-benzyl-5-C-benzyloxymethyl-1,2,3,4-cyclohexane tetrol (35 mg, 91.7%).

1D-(1,2,4/3,5)-1-amino-2,3,4-tri-O-benzyl-5-C-benzyloxymethyl-1,2,3,4-cyclohexane tetrol can be used in a method of synthesis similar to that provided above for the synthesis of valienamine-1,6-anhydroglucose and valienamine-glucose hydrochloride to synthesize validamine-1,6-anhydroglucose and validamine-glucose hydrochloride.

The syntheses outlined in Examples 50–52 are also reported in U.S. patent application Ser. No. 08/481,645 filed concurrently herewith as attorney docket no. 000475-052 and entitled MODIFIED KOJIBIOSIDES ANALOGUES which application is incorporated herein by reference in its entirety.

Example 50

Synthesis of 1,5-trans-(α-D)-C-glucopyranosyl-amino-(glucose)

A. Synthesis of 1-C-tosyloxymethyl-2,3,4,6-tetra-O-benzyl-1,5-trans(α-D)-C-glucopyranoside To a solution of 1-C-hydroxymethyl-1,5-trans(α-D)-C-2,3,4,6-tetra-O-benzylglucopyranose (526 mg) in dry pyridine (5.0 mL) was added p-toluene-sulfonyl chloride (270 mg) and the reaction mixture was stirred for 15 hours at room temperature. The reaction mixture was evaporated and the residue purified by chromatography on silica gel column using hexane-ethyl acetate (3:1) as eluent to provide for 1-C-tosyloxymethyl-2,3,4,6-tetra-O-benzyl-1,5-trans(α-D)-C-glucopyranoside (613 mg).

B. Synthesis of 1-C-azidomethyl-2,3,4,6-tetra-O-benzyl-1,5-trans(α-D)-C-glucopyanoside To a solution of 1-C-tosyloxymethyl-2,3,4,6-tetra-O-benzyl-1,5-trans(α-D)-C-glucopyranoside (588mg) in DMF (10.0 mL), sodium azide (380 mg) was added and the reaction mixture was then heated at 80° C. for 15 hours. Solvent was evaporated from the mixture under high vacuum and the product was purified by chromatography on silica gel using hexane:ethyl acetate (10:1) as eluent to provide 1-C-azidomethyl-2,3,4,6-tetra-O-benzyl-1,5-trans (α-D)-C-glucopyanoside (420 mg); [α]D+30° (C 0.735, $CHCl_3$).

C. Synthesis of 1-C-methyl amino-2,3,4,6-tetra-O-benzyl-1,5-trans(α-D)-C-glucopyranoside 1-C-azidomethyl-2,3,4,6-tetra-O-benzyl-1,5 trans(α-D)-C glucopyanoside (391 mg) was dissolved in a mixture of pyridine-water -triethylamine (26:4:0.8, 10 mL). A stream of hydrogen sulfide was bubbled at 0° C. for 1 hour and then allowed to warm at room temperature. After bubbling for 5 hours at room temperature, hydrogen sulfide was filled at 0° C. for 15 minutes and stirred at room temperature for 15 hours. The mixture was evaporated to dryness and coevaporated with toluene (3×50 mL) and purified by chromatography on silica gel using chloroform-methanol (9:1) as eluent to obtain 1-C-methyl amino-2,3,4,6-tetra-O-benzyl-1,5-trans(α-D)-C glucopyranoside (380 mg).

D. Synthesis of 2,3,4,6-tetra-O-benzyl-1,5-trans-(α-D)-C-amino-(1,6-anhydro-4-O-benzyl-glucopyranose A solution of 1-C-methyl amino-2,3,4,6-tetra-O-benzyl-1,5-trans(α-D)-C glucopyranoside (380 mg) and 1,6-anhydro-4-O-benzyl-2,3-epoxy-glucose made according to the method set forth in Cerny et al, J. Czechosl. Chem. Commun. 39 (1974) (937 mg) in n-propanol (6.0 mL) was heated at 90° C. for 3 days. Solvent was evaporated, then co-evaporated with toluene and the residue was chromatographed on a silica gel column using chloroform-ethyl acetate (2:1) as eluent to obtain (320 mg) 2,3,4,6-tetra-O- benzyl-1,5-trans-(α-D)-C-1-methyl-amino-(1,6-anhydro-4-O-benzyl-glucopyranose.

E. Synthesis of 1,5-trans-(α-D)-C-glucopyranosyl-1-methylamino-(1,6-anhydro)glucopyranose 2,3,4,6-tetra-O-benzyl-1,5-trans-(α-D)-C-1-methyl-amino-(1,6-anhydro-4-O-benzyl-glucopyranose (361 mg, 0.46 mmol) was dissolved in a mixture of methanol-acetic acid (20:1, 10 mL) and 5% palladium on carbon (360 mg) was added. 0.46 mmol of hydrochloric acid was also added and stirred the reaction mixture for 3 hours at room temperature at one atmospheric pressure. Filtered the catalyst on the pad of celite and evaporated to dryness. Compound was purified by chromatography on silica gel using dichloromethane-methanol-water (65:35:5) as eluent which was further purified by Sephadex column filtration using ethanol-water (1:1) as eluent to provide 1,5-trans-α-D-C-glucopyranosyl-1-methylamino-(1,6-anhydro)glucopyranose (148 mg, 86.4%).

F. Synthesis of 1,5-trans-(α-D)-C-glucopyranosyl-1-methyl amino-(glucose)

1,5-trans-(α-D)-C-glucopyranosyl-1-methylamino-(1,6-anhydro-glucopyranose (115 mg, 0.31 mmol) was heated at 100° C. in 2N HCl solution for 4 days. Solvent was removed by co-evaporation with water and the residue was purified by chromatography on Iatrobeads using chloroform-methanol-water (65:35:5) as eluent to provide for the title compound (82 mg, 68%).

Example 51

Synthesis of methyl-2-O-[1,5-trans-(α-D)-C-glucopyranosyl]-α-D-glucopyranoside

A. Synthesis of 1-C-hydroxytrifluoromethane sulfonyl-1,5-trans-(α-D)-C-2,3,4,6-tetra-O-benzylglucopyranose 1-C-hydroxymethyl-1,5-trans-(α-D)-C-2,3,4,6-tetra-O-benzyl-glucopyranose (670 mg, 1.21 mmol) was dissolved in dichloromethane (5.5 mL) and pyridine (294 µL) was added. At −20° C. triflic anhydride (2.5 mL) was added and stirred the reaction mixture for 45 minutes at this temperature. Diluted the reaction mixture with dichloromethane (100 mL) and washed with saturated solution of sodium bicarbonate (2×100 mL) and water (2×100 mL), dried over sodium sulfate, filtered and evaporated to dryness which was used directly for the next reaction.

B. Synthesis of methyl-2-O-[1,5-trans-(α-D)-C-2,3,4,6-tetra-O-benzylglucopyranosyl]-3-O-benzyl-4,6-O-benzylidene-α-D-glucopyranoside Methyl-3-O-benzyl-4,6-O-benzylidene-α-D-glucopyranoside (185 mg, 0.50 mmol) was dissolved in anhydrous THF and cooled to 0° C. 1 molar solution of [(CH$_3$)$_3$Si]$_2$NLi (1.49 mmol) was added in THF dropwise. It was stirred for 1 h at 0° C. and 2 days at room temperature. Compound was evaporated and purified by chromatography on silica gel using hexane-ethyl acetate (4:1) as eluent to give methyl-2-O-[1,5-trans-(α-D)-C-2,3,4,6-tetra-O-benzylglucopyranosyl]-3-O-benzyl-4,6-O-benzylidene-α-D-glucopyranoside (60 mg).

C. Synthesis of methyl-2-O-[1,5-trans-(α-D)-C-glucopyranosyl]-α-D-glucopyranoside Methyl-2-O-[1,5-trans-(α-D)-C-2,3,4,6-tetra-O-benzylglucopyranosyl]-3-O-benzyl-4,6-O-benzylidene-α-D-glucopyranoside (50.0 mg) was hydrogenated as described earlier using 5% palladium on carbon (50 mg) in methanol (5.0 mL). After the usual work up, methyl-2-O-[1-C-hydroxymethyl-1,5-trans-(α-D)-C-glucopyranosyl]-α-D-glucopyranoside (20 mg) was obtained after lyophilization.

Example 52

Synthesis of homonojirimycin-glucose

A. Synthesis of protected homonojirimycin

Fully protected N-benzyl-tetra-O-benzyl-homonojirimycin (prepared according to the literature Liu et al., J. Org. Chem., Vol 51, No. 21, 1987) (128 mg) was dissolved in toluene (1.5 mL) and added to it triphenylphosphine (226 mg) followed by addition of hydrazoic acid (12.5 mL) solution in benzene (10%) and DEAD (14.2 µL). The reaction mixture was stirred at room temperature for 2.5 h. Diluted with CH$_2$Cl$_2$ (50 mL) washed with water (2×50 mL), dried over Na$_2$SO$_4$ and evaporated. The syrup was purified by chromatography on silica gel using hexane-ethyl acetate (10:1) as eluent to obtain the azido derivative of homonojirimycin (112 mg).

B. Synthesis of N-benzyl-tetra-O-benzyl-amino-derivative of homonojirimycin

The product of A) above (112 mg) was dissolved in a mixture of pyridine-water-triethyl amine (26:4:0.8, 10.0 mL) and cooled to 0° C. for 1 h and stirred overnight at room temperature. The reaction mixture was evaporated, co-evaporated with toluene and purified by chromatography on silica gel using chloroform-ethyl acetate (1:1) as eluent to give N-benzyl-tetra-O-benzyl-amino-derivative of homonojirimycin (48.0 mg).

C. Synthesis of protected homonojirimycin-amino-1,6-anhydroglucose

A solution of N-benzyl-tetra-O-benzyl-amino-derivative of homonojirimycin (48 mg, 0.72 mmol) and 1,6-anhydro-4-O-benzyl-2,3-epoxy-glucose (100 mg) in n-propanol was stirred at 90° C. for 2 days. Evaporated the reaction mixture and purified by chromatography on silica gel using hexane-ethyl acetate (3:1) as eluent. Pure product (43 mg) was obtained.

D. Synthesis of homonojirimycin-1,6-amino-anhydroglucose

The compound prepared in C above (43 mg) was dissolved in methanol (3.0 mL) and 1.1 equivalents of hydrochloric acid and 5% palladium on carbon (43 mg) was added. Stirred the reaction mixture for 15 h at one atmospheric pressure and room temperature. Purification, after usual workup, by chromatography on silica gel chloroform-methanol-water (60:40:5) as eluent provided homonojirimycin-1,6-anhydroglucose (19 mg).

E. Synthesis of homonojirimycin-amino-glucose

Homonojirimycin-amino-1,6-anhydroglucose (15 mg) was heated at 100° C. in 2N HCl solution for 4 days. Solvent was removed by evaporation with water and the residue was purified by chromatography on an Iatrobead column using chloroform-methanol-water (60:40:5) as eluent to provide the title compound (8.0 mg) after lyophilization.

Example 53

Biological Results

Some of the compounds which are modified analogues of the trisaccharides corresponding to the end tail of precursor oligosaccharides Glc$_3$Man$_9$GlcNAc$_2$-PP-Dol, were evaluated as inhibitors of glucosidase I activity. Glucosidase I was purified by a literature procedure as follows. To prepare an affinity matrix, carboxypentyl-deoxynojirimycin was coupled with Affigel 102 according to Shailubhai et al[19]. Glucosidase I was solubilized from calf pancreas microsomes, and purified from glucosidase II activity by affinity chromatography according to the same authors.

Substrates for Assay of Glucosidase I $^{14}$C-labelled Glc$_3$Man$_9$GlcNAc$_2$-PP-Dol was prepared by the incubation of UDP-[$^{14}$C]Glc with calf pancreas microsomes as described by Herscovien et al[40]. Glc$_3$Man$_9$GlcNAc$_2$ was released by mild acid hydrolysis and purified by BioGel P4 chromatography.

Assay for Glucosidase I Activity

Affinity purified glucosidase I was assayed as described by Saunier et al.[41] by adsorption of undigested substrate and oligosaccharide product to ConA-Sepharose and scintillation counting of [$^{14}$C]Glc in the column eluent. Oligosaccharides as potential inhibitors were evaluated using castanospermine as a baseline inhibitor.

Results

Following the procedures set forth above, compound 40 was a very good inhibitor of glycosidase I activity (100% at 1 mM concentration). The 3" and 4"-deoxy trisaccharides 45 and 48 showed 50% and 79% activity at 1 mM concentration. However, when the 2"-OH group in trisaccharide 40 was replaced by fluoro, deoxy, methoxy and amino functional groups, the activity was completely eliminated as was the activity for the 6" deoxy compound 49.

The results from different trisaccharides suggest that reduction of the glucose residue to 3" or 4"-deoxy is well tolerated for binding to the active site, whereas substituents at C-2 of the same residue are not well tolerated. Conformation of the glucotriose unit in the lipid-linked oligosaccharide precursor for protein glycosylation was determined by Ballow et al.[22] on the model tetrasaccharide αGlc(1-2) αGlc(1-3)αGlc(1-3)αMan-O-(CH$_2$)$_2$CH$_3$ dissolved in deuterated dimethylsulfoxide. The hydroxyl proton on C-2 of the non-reducing end glucose and on C-4 of the glucose attached to mannose both show dramatic shifts indicative of a strong hydrogen bond between these two hydroxyl groups. Activity of the trisaccharide is eliminated by modifying at the 2"-OH group with F, OMe, deoxy and amino.

While the invention has been described in terms of various preferred embodiments, the skilled artisan will appreciate that various modification, substitutions, omissions and changes may be made without departing from the spirit thereof. The descriptions of subject matter in this disclosure are illustrative of the invention and are not intended to be construed as limitations upon the scope of the invention.

What is claimed is:

1. A compound useful in the synthesis of modified trisaccharide α-glucosidase I inhibitors represented by Formula I:

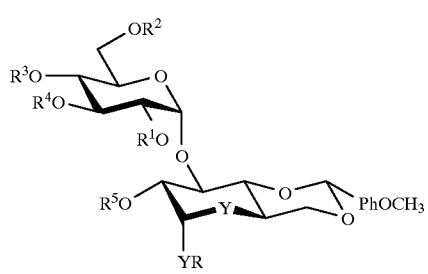

wherein each Y is independently selected from the group consisting of —O— and NH, R is an aglycon of from 1 to 20 carbon atoms, R$^1$ is selected from the group consisting of —CH$_2$CH=CH$_2$ and hydrogen, and R$^2$, R$^3$, R$^4$ and R$^5$ are protecting groups capable of being differentially removed as compared to —O—CH$_2$CH=CH$_2$.

2. The compound of claim 1 wherein R$^2$, R$^3$, R$^4$ and R$^5$ are benzyl and R$^1$ is hydrogen.

3. The compound of according to claim 2 wherein each Y is —O—.

4. A compound useful in the synthesis of modified trisaccharide α-glucosidase I inhibitors represented by Formula II:

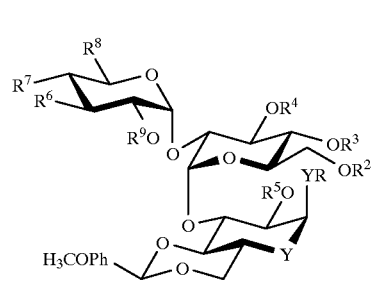

wherein each Y is independently selected from the group consisting of —O— and —NH—, R is an aglycon of from 1 to 20 carbon atoms, R$^2$, R$^3$, R$^4$ and R$^5$ are protecting groups, R$^6$ and R$^7$ are independently selected from the group consisting of —O—Pr, hydrogen, fluoro, azido, and —OCH$_3$ where Pr is a protecting group, R$^8$ is selected from the group consisting of —CH$_2$—O—Pr, CH$^2$—OH, —CH$_2$—H, —CH$_2$—fluoro, —CH$_2$-azido and —CH$_2$—OCH$_3$ where Pr is a protecting group, and R$^9$ is selected from the group consisting of hydrogen and a protecting group.

5. The compound of claim 4 wherein R$^6$, R$^7$ and R$^8$ are selected as set forth below:

| R$_6$ | R$_7$ | R$_8$ |
|---|---|---|
| OBn | OBn | OBn |
| H | OBn | OBn |
| OAc | OAc | OAc |
| OH | OH | OH |
| H | OBn | OBn |
| OMe | OBn | OBn |
| OBn | H | OBn |
| OBn | OMe | OBn | wherein Bn is benzyl and Ac is acetyl.

6. A compound represented by Formula III:

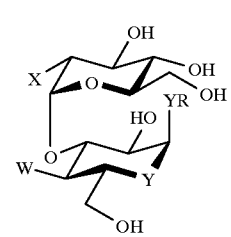

wherein each Y is independently selected from the group consisting of O and NH and X is selected from the group consisting of xylose, valienamine, validamine, valiolamine, 5-deoxy-5-thioglucose, homonorijimycin, 1,5-trans-(C)-glucopyranosylamine and a compound of the formula:

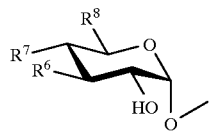

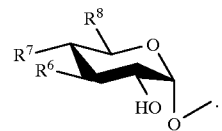

wherein $R^6$ and $R^7$ are independently selected from the group consisting of —O—Pr, hydrogen, fluoro, azido, and —OCH$_3$ where Pr is a protecting group, $R^8$ is selected from the group consisting of —CH$_2$—O—Pr, —CH$_2$—H, —CH$_2$—fluoro, —CH$_2$-azido and —CH$_2$—OCH$_3$ where Pr is a protecting group, W is selected from the group consisting of hydrogen, hydroxyl, alkoxy of from 1 to 4 carbon atoms, fluoro, chloro, and amino; and R is an aglycon of from 1 to 20 carbon atoms and which compounds inhibit the glucosidase activity.

7. A pharmaceutical composition comprising a pharmaceutically inert carrier and from 0.1 to 95 weight percent of a compound according to claim 5.

8. The compound of claim 6 wherein R is —(CH$_2$)$_8$COOCH$_3$ and W is —OH and X is a compound of the formula:

9. The compound of claim 8 wherein each Y is oxygen.

10. The compound of claim 9 wherein $R^6$ is hydrogen, $R^7$ is hydroxyl and $R^8$ is hydroxyl.

11. The compound of claim 9 wherein $R^6$ is methoxy, $R^7$ is hydroxyl and $R^8$ is hydroxyl.

12. The compound of claim 9 wherein $R^6$ is hydroxyl, $R^7$ is hydrogen and $R^8$ is hydroxyl.

13. The compound of claim 9 wherein $R^6$ is hydroxyl, $R^7$ is methoxy and $R^8$ is hydroxyl.

14. The compound of claim 9 wherein R is hydroxyl, R is hydroxyl and R is methyl.

* * * * *